United States Patent
Yokoyama et al.

(10) Patent No.: US 9,444,055 B2
(45) Date of Patent: Sep. 13, 2016

(54) ORGANIC ELECTROLUMINESCENT DEVICE

(75) Inventors: Norimasa Yokoyama, Tokyo (JP);
Shuichi Hayashi, Tokyo (JP); Eiji Takahashi, Ibaraki (JP); Shigeru Kusano, Ibaraki (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 453 days.

(21) Appl. No.: 14/001,560

(22) PCT Filed: Feb. 24, 2012

(86) PCT No.: PCT/JP2012/054605
§ 371 (c)(1),
(2), (4) Date: Aug. 26, 2013

(87) PCT Pub. No.: WO2012/117973
PCT Pub. Date: Sep. 7, 2012

(65) Prior Publication Data
US 2013/0328040 A1    Dec. 12, 2013

(30) Foreign Application Priority Data
Feb. 28, 2011  (JP) .................................. 2011-042169

(51) Int. Cl.
*H01L 51/50*    (2006.01)
*H01L 51/00*    (2006.01)
(Continued)

(52) U.S. Cl.
CPC ......... *H01L 51/0072* (2013.01); *C07C 211/54* (2013.01); *C07C 211/56* (2013.01); *C07C 211/58* (2013.01); *C09K 11/06* (2013.01);
(Continued)

(58) Field of Classification Search
None
See application file for complete search history.

(56) References Cited

U.S. PATENT DOCUMENTS

| | | | |
|---|---|---|---|
| 4,720,432 A | 1/1988 | Vanslyke et al. | |
| 5,639,914 A | 6/1997 | Tomiyama et al. | |

(Continued)

FOREIGN PATENT DOCUMENTS

| | | |
|---|---|---|
| JP | 6-314594 | 11/1994 |
| JP | 7-126615 | 5/1995 |

(Continued)

OTHER PUBLICATIONS

Christoph Jonda et al., "Investigation of TDAPBs as hole-transporting materials for organic light-emitting devices (OLEDs)", Advanced Materials for Optics and Electronics, vol. 9, No. 3, XP55132268, May 1, 1999, pp. 117-128.

(Continued)

*Primary Examiner* — Gregory Clark
(74) *Attorney, Agent, or Firm* — Greenblum & Bernstein, P.L.C.

(57) ABSTRACT

An organic electroluminescent device comprising, between an anode and a cathode, a hole-transporting layer, a luminous layer and an electron-transporting layer, wherein the hole-transporting layer contains an arylamine compound (X) having a molecular structure to which three or more triphenylamine skeletons are singly bonded or bonded through a divalent hydrocarbon group and an arylamine compound (Y) having a molecular structure to which two triphenylamine skeletons are singly bonded or bonded through the divalent hydrocarbon group. The device excels in hole and electron injection/transport property, stability and durability in the form of thin films, and is highly efficient, becomes luminous on a low driving voltage, and has a long life.

6 Claims, 1 Drawing Sheet

8: CATHODE
7: ELECTRON INJECTION LAYER
6: ELECTRON TRANSPORTING LAYER
5: LUMINOUS LAYER
4: HOLE TRANSPORTING LAYER
3: HOLE INJECTION LAYER
2: TRANSPARENT ANODE
1: GLASS SUBSTRATE

(51) Int. Cl.
  *C09K 11/06* (2006.01)
  *H05B 33/14* (2006.01)
  *C07C 211/54* (2006.01)
  *C07C 211/56* (2006.01)
  *C07C 211/58* (2006.01)
  *H05B 33/10* (2006.01)

(52) U.S. Cl.
  CPC ......... *H01L51/0059* (2013.01); *H05B 33/10* (2013.01); *H05B 33/14* (2013.01); *C07C 2101/14* (2013.01); *C07C 2103/18* (2013.01); *C09K 2211/1007* (2013.01); *C09K 2211/1011* (2013.01); *C09K 2211/1014* (2013.01); *C09K 2211/1029* (2013.01); *H01L 2251/308* (2013.01)

(56) References Cited

U.S. PATENT DOCUMENTS

| | | | |
|---|---|---|---|
| 5,707,747 | A | 1/1998 | Tomiyama et al. |
| 5,792,557 | A | 8/1998 | Nakaya et al. |
| 7,357,992 | B2 | 4/2008 | Kato et al. |
| 7,375,250 | B2 | 5/2008 | Saitoh et al. |
| 7,402,701 | B2 | 7/2008 | Kato et al. |
| 8,173,272 | B2 | 5/2012 | Jang et al. |
| 2006/0125378 | A1 | 6/2006 | Saitoh et al. |
| 2006/0182994 | A1* | 8/2006 | Sakamoto ............ C07C 211/54 428/690 |
| 2009/0134781 | A1 | 5/2009 | Jang et al. |
| 2011/0073852 | A1 | 3/2011 | Yokoyama et al. |
| 2012/0161107 | A1 | 6/2012 | Yokoyama et al. |
| 2012/0292609 | A1 | 11/2012 | Yokoyama et al. |

FOREIGN PATENT DOCUMENTS

| | | |
|---|---|---|
| JP | 8-48656 | 2/1996 |
| JP | 08-291115 | 11/1996 |
| JP | 11-260559 | 9/1999 |
| JP | 2001-114735 | 4/2001 |
| JP | 3194657 | 6/2001 |
| JP | 2001-273978 | 10/2001 |
| JP | 2002-053533 | 2/2002 |
| JP | 2005-15419 | 1/2005 |
| JP | 2005-108804 | 4/2005 |
| JP | 2009-530371 | 8/2009 |
| WO | 2006/121237 | 11/2006 |
| WO | 2009/139475 | 11/2009 |
| WO | 2009/151039 | 12/2009 |
| WO | 2011/093056 | 8/2011 |

OTHER PUBLICATIONS

Lian Duan et al., "Solution processable small molecules for organic light-emitting diodes", Journal of Materials Chemistry, vol. 20, No. 31, XP55127738, Jan. 1, 2010, pp. 6392.

Von Malm N et al., "Distribution of occupied states in doped organic hole transport materials", Synthetic Metals Elsevier Sequoia, Lausanne, CH, vol. 126, No. 1, XP027380789, Jan. 28, 2002, pp. 87-95.

Fang Q et al., "A novel fluorene derivative containing four triphenylamine groups: Highly thermostable blue emitter with hole-transporting ability for organic light-emitting diode (OLED) ", Synthetic Metals, Elsevier Sequoia, Lausanne, CH, vol. 155, No. 1, XP027758275, Oct. 15, 2005, pp. 206-210.

Search Report from E.P.O. in EP12752444.5, dated Aug. 7, 2014.

U.S. Appl. No. 14/008,708 to Norimasa Yokoyama et al., filed Sep. 30, 2013.

U.S. Appl. No. 14/000,406 to Norimasa Yokoyama et al., filed Aug. 20, 2013.

International Search Report mailed May 1, 2012 in PCT/JP2012/054605.

* cited by examiner

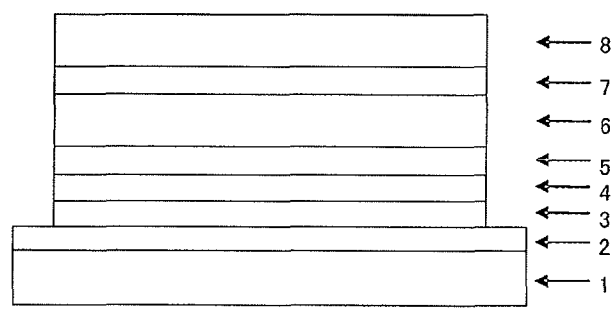
8: CATHODE
7: ELECTRON INJECTION LAYER
6: ELECTRON TRANSPORTING LAYER
5: LUMINOUS LAYER
4: HOLE TRANSPORTING LAYER
3: HOLE INJECTION LAYER
2: TRANSPARENT ANODE
1: GLASS SUBSTRATE

ORGANIC ELECTROLUMINESCENT DEVICE

TECHNICAL FIELD

This invention relates to an organic electroluminescent device which is a spontaneously luminescent device suited for use in various kinds of display devices. More specifically, the invention relates to an organic electroluminescent device (hereinafter often abbreviated as organic EL device) using specific arylamine derivatives.

BACKGROUND ART

An organic EL device is a spontaneously luminous device which features higher brightness and higher legibility than those of the liquid crystal devices enabling vivid display to be attained and has, therefore, been vigorously studied.

In 1987, C. W. Tang et al. of the Eastman Kodak Co. have developed a device of a layer-laminated structure comprising various kinds of materials to bear individual roles, and have put an organic EL device using organic materials into a practical use. The above device is constituted by laminating layers of a phosphorescent body capable of transporting electrons and an organic material capable of transporting holes. The device is capable of attaining a brightness of as high as 1000 cd/m$^2$ or more with a voltage of not higher than 10 V by injecting the above two kinds of electric charges into the layer of the phosphorescent body to emit light (see patent documents 1 and 2).

So far, many improvements have been made to put the organic EL device to practical use. For example, the organic EL device has been widely known having a structure comprising an anode, a hole injection layer, a hole-transporting layer, a luminous layer, an electron-transporting layer, an electron injection layer and a cathode which are arranged in this order on a substrate more finely dividing their roles than ever before. The device of this kind is achieving a high efficiency and a high durability.

To further improve the luminous efficiency, attempts have been made to utilize triplet excitons and study has been forwarded to utilize a phosphorescent luminous compound.

In the organic EL device, the electric charges injected from the two electrodes recombine together in the luminous layer to emit light. Here, to improve the luminous efficiency, to lower the driving voltage and to lengthen the life, it is necessary that the device has excellent carrier balance enabling the electrons and holes to be efficiently injected and transported, and enabling them to be efficiently recombined together.

As the hole injection material used for the organic EL device, there were, first, proposed phthalocyanines such as copper phthalocyanine (CuPc) (e.g., see a patent document 3), but materials having a phenylenediamine structure have now been widely used (see a patent document 4) because they have an absorption in the visible band.

As the hole-transporting material, on the other hand, arylamine materials having a benzidine skeleton have heretofore been used (see a patent document 5).

Tris(8-hydroxyquinoline) aluminum (Alq$_3$) which is a representative luminous material has been generally used as the electron-transporting material. However, the electron mobility of the Alq$_3$ is lower than that of the hole-transporting material that is generally used. Besides, the work function of the Alq$_3$ is 5.8 eV which cannot be said to be a sufficiently large hole blocking power. Therefore, use of the above hole-transporting material is accompanied by a problem in that the holes partly pass through the luminous layer to deteriorate the efficiency.

In order to efficiently inject the holes or the electrons from the anode and cathode into the luminous layer, further, there has been developed a device obtained by laminating the hole injection layers and the electron injection layers each in a number of two or more layers to set stepwise the ionization potential values and the values of electron affinity possessed by the materials (see a patent document 6). With the materials that are used, however, none of the luminous efficiency, driving voltage or device life is still satisfactory.

Further, with the conventional organic EL devices, the hole-transporting layer usually consists of a very thin film. Therefore, the conventional organic EL devices are affected by the surface roughness of the transparent electrode such as ITO electrode which is used as the anode and a probability of producing defective products is high due to short-circuiting of the fabricated devices. In this case, an increase in the thickness of the hole-transporting layer can conceal the surface roughness of the anode such as ITO electrode and can decrease the probability of producing defective devices that are fabricated. However, the driving voltage increases with an increase in the thickness of the hole-transporting layer and may exceed a practical driving voltage. Namely, it becomes difficult to emit light with the practical driving voltage.

In order to improve characteristics of the organic EL device and to improve the yield of the device production, it has been desired to develop a device that features a high luminous efficiency, a low driving voltage and a long life by using in combination the materials that excel in hole and electron injection/transport property, stability and durability in the form of thin films, permitting holes and electrons to be highly efficiently recombined together.

Further, in order to improve characteristics of the organic EL device, it has been desired to develop a device that maintains carrier balance and features a high efficiency, a low driving voltage and a long life by using in combination the materials that excel in hole and electron injection/transport property, and stability and durability in the form of thin films.

PRIOR ART DOCUMENTS

Patent Documents

Patent document 1: JP-A-8-48656
Patent document 2: Japanese Patent No. 3194657
Patent document 3: U.S. Pat. No. 4,720,432
Patent document 4: JP-A-8-291115
Patent document 5: Japanese Patent No. 3529735
Patent document 6: JP-A-6-314594
Patent document 7: JP-A-7-126615
Patent document 8: JP-A-8-048656
Patent document 9: JP-A-2005-108804

OUTLINE OF THE INVENTION

Problems that the Invention is to Solve

The object of the present invention is to provide an organic EL device that features a high efficiency, a low driving voltage and a long life by using in combination various kinds of materials for organic EL device that excel in hole and electron injection/transport property, and stability and durability in the form of thin films so that the properties possessed by the respective materials can be effectively exhibited.

Means for Solving the Problems

To achieve the above object, therefore, the present inventors have paid attention to that the arylamine type materials have excellent hole injection and transporting properties, stability and durability in the form of thin films, have selected two kinds of specific arylamine compounds, have fabricated various organic EL devices by so combining the arylamine compounds that the holes could be efficiently injected and transported into the luminous layer, and have keenly evaluated the properties of the devices. As a result, the present invention was completed.

According to the present invention, there is provided an organic electroluminescent device comprising, between an anode and a cathode, a hole-transporting layer, a luminous layer and an electron-transporting layer, wherein the hole-transporting layer contains an arylamine compound (X) having a molecular structure to which three or more triphenylamine skeletons are singly bonded or bonded through a divalent hydrocarbon group and an arylamine compound (Y) having a molecular structure to which two triphenylamine skeletons are singly bonded or bonded through a divalent hydrocarbon group.

In the organic electroluminescent device of the invention, it is desired that the arylamine compound (X) is represented by the following general formula (1).

[Chemical 1]

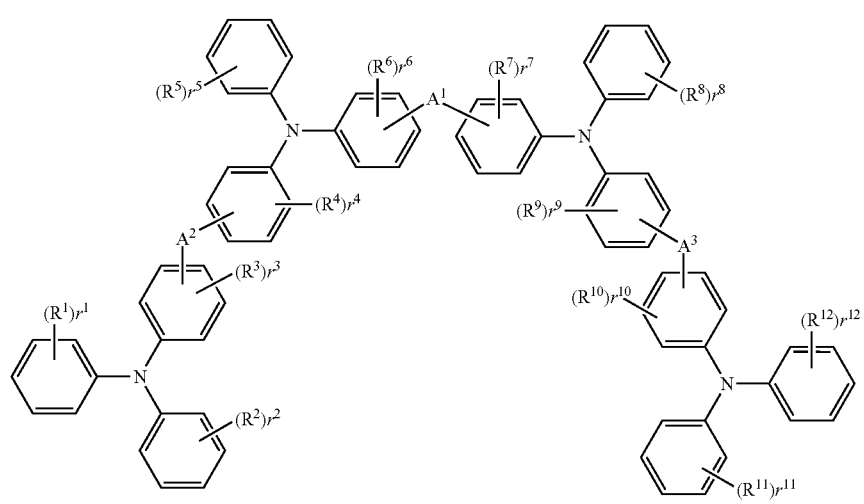

(1)

wherein,
$r^1$ to $r^{12}$, respectively, represent the numbers of $R^1$ to $R^{12}$, $r^1$, $r^2$, $r^5$ $r^8$, $r^{11}$ and $r^{12}$ being integers of 0 to 5, and $r^3$, $r^4$, $r^6$, $r^7$, $r^9$ and $r^{10}$ being integers of 0 to 4,
$R^1$ to $R^{12}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups, or unsubstituted or substituted aromatic heterocyclic groups and among these groups, the groups bonded to the same benzene ring may be bonded together to form a ring, and $A^1$ to $A^3$, respectively, are single bonds or divalent hydrocarbon groups represented by the following structural formulas (B) to (F).

[Chemical 2]

(B)

(wherein $n1$ is an integer of 1 to 3)

[Chemical 3]

(C)

-continued

[Chemical 4]

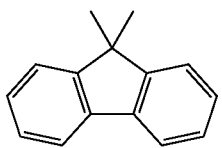

(D)

[Chemical 5]

(E)

[Chemical 6]

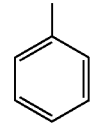
(F)

In the arylamine compound (X) represented by the above general formula (1), it is desired that at least one of $R^1$ to $R^{12}$ is a deuterium atom or a group that contains deuterium atoms.

In the invention, further, it is desired that the arylamine compound (Y) is represented by the following general formula (2).

[Chemical 7]

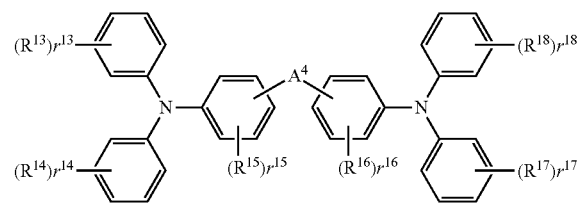
(2)

wherein, $r^{13}$ to $r^{18}$, respectively, represent the numbers of $R^{13}$ to $R^{18}$, $r^{13}$, $r^{14}$, $r^{17}$ and $r^{18}$ being integers of 0 to 5, and $r^{15}$ and $r^{16}$ being integers of 0 to 4, $R^{13}$ to $R^{18}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups, or unsubstituted or substituted aromatic heterocyclic groups and among these groups, the groups bonded to the same benzene ring may be bonded together to form a ring, and $A^4$ represents a single bond or a divalent hydrocarbon group represented by the above structural formulas (B) to (F).

In the arylamine compound (Y) represented by the above general formula (2), it is desired that at least one of $R^{13}$ to $R^{18}$ is a deuterium atom or a group that contains deuterium atoms.

In the above organic EL device of the present invention, it is desired that the arylamine compound (X) and the arylamine compound (Y) are contained in the hole-transporting layer at a weight ratio of X:Y=1:9 to 6:4, more desirably, 1:9 to 4:6, and most desirably, 1:9 to 2:8.

Effects of the Invention

The organic EL device of the present invention has a distinguished feature in that the hole-transporting layer is formed by using the arylamine compound (X) that has three or more triphenylamine skeletons in a molecule thereof and the arylamine compound (Y) that has two triphenylamine skeletons in a molecule thereof.

Namely, the hole-transporting layer that contains the arylamine compounds (X) and (Y) in combination shows a high hole drift speed, maintains stability in the form of a thin film, and has excellent heat resistance.

Therefore, the organic EL device of the invention permits holes to be efficiently injected and transported into the luminous layer from the hole-transporting layer, shows a high luminous efficiency, drives on a low voltage and, as a result, realizes a long service life.

BRIEF DESCRIPTION OF THE DRAWING

FIG. 1 is a view showing the constitution of organic EL devices of Examples 1 to 6 and Comparative Examples 1 to 5.

MODES FOR CARRYING OUT THE INVENTION

The organic EL device of the present invention has a basic structure in which a hole-transporting layer, a luminous layer and an electron-transporting layer are formed in this order between an anode and a cathode and, specifically, has a structure in which the hole-transporting layer is formed by using two kinds of arylamine compounds (X) and (Y) having triphenylamine skeletons.

Described below are the layers constituting the organic EL device.

<Anode>

The anode is formed by vacuum evaporation on a transparent substrate such as transparent plastic substrate (e.g., polyethylene terephthalate substrate) or glass substrate by using an electrode material having a large work function, such as ITO or gold.

<Hole-Transporting Layer>

As described already, the hole-transporting layer positioned on the side of the anode relative to the luminous layer contains the two kinds of arylamine compounds (X) and (Y) having triphenylamine skeletons.

Arylamine Compound (X):

The arylamine compound (X) has three or more triphenylamine skeletons which are singly bonded or bonded through a divalent hydrocarbon group (i.e., a divalent group having no hetero atom). The arylamine compound (X) has a higher hole mobility than that of the arylamine compound (Y) that will be described later.

The arylamine compound (X) is, for example, a trimer or a tetramer of various triphenylamines and is, preferably, the one having four triphenylamine skeletons from the standpoint of having a specifically high hole mobility. The arylamine having the four triphenylamine skeletons can be the one represented by the following general formula (1).

[Chemical 8]

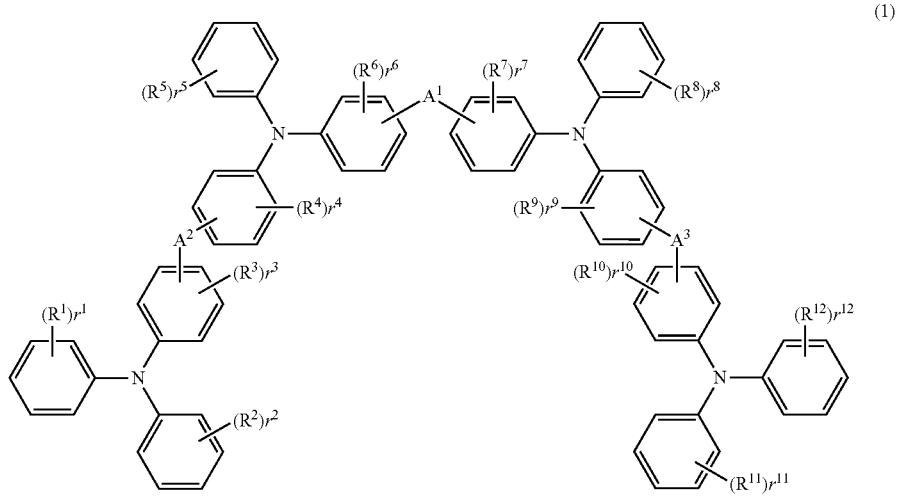

(1)

In the above general formula (1), $r^1$ to $r^{12}$ are the numbers of the groups $R^1$ to $R^{12}$ that can bond to the benzene rings in the molecule, $r^1$, $r^2$, $r^5$, $r^8$, $r^{11}$ and $r^{12}$ being integers of 0 to 5, and $r^3$, $r^4$, $r^6$, $r^7$, $r^9$ and $r^{10}$ being integers of 0 to 4. Namely, the values $r^1$ to $r^{12}$ that are 0s mean that none of the groups $R^1$ to $R^{12}$ have been bonded to the benzene rings.

The groups $R^1$ to $R^{12}$ may or may not be the same, and are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups, or unsubstituted or substituted aromatic heterocyclic groups. Further, if some of the groups $R^1$ to $R^{12}$ are present in plural numbers ($r^1$ to $r^{12}$ are 2 or more), they may be bonded together to form a ring.

Among the above groups $R^1$ to $R^{12}$, the unsubstituted alkyl group having 1 to 6 carbon atoms may be of the form of a straight chain or may be branched, such as methyl group, ethyl group, n-propyl group, isopropyl group, n-butyl group, isobutyl group, tert-butyl group, n-pentyl group, isopentyl group, neopentyl group or n-hexyl group.

The unsubstituted alkenyl group having 2 to 6 carbon atoms, too, may be of the form of a straight chain or may be branched, such as vinyl group, allyl group, isopropenyl group and 2-butenyl group.

As the aromatic hydrocarbon group, there can be exemplified phenyl group, biphenylyl group, terphenylyl group, tetrakisphenyl group, styryl group, naphthyl group, anthryl group, acenaphthenyl group, fluorenyl group, phenanthryl group, and indenyl group and pyrenyl group.

As the aromatic heterocyclic group, there can be exemplified pyridyl group, pyrimidyl group, furyl group, pyrrolyl group, thienyl group, quinolyl group, isoquinolyl group, benzofuranyl group, benzothienyl group, indolyl group, carbazolyl group, benzoxazolyl group, benzothiazolyl group, quinoxalyl group, benzoimidazolyl group, pyrazolyl group, dibenzofuranyl group, dibenzothienyl group, naphthyridinyl group, phenanthrolinyl group and acrydinyl group.

Further, the above alkenyl group, aromatic hydrocarbon group and aromatic heterocyclic group may all have a substituent such as deuterium atom, fluorine atom, chlorine atom, trifluoromethyl group, alkyl group having 1 to 6 carbon atoms, phenyl group, biphenylyl group, terphenylyl group, tetrakisphenyl group, styryl group, naphthyl group, fluorenyl group, phenanthryl group, indenyl group or pyrenyl group. These substituents may, further, have other substituents.

Further, if some of the groups $R^1$ to $R^{12}$ are present in plural numbers and are bonded together to form ring, they may be singly bonded together to form a ring or may be bonded together via a methylene group that may have a substituent, or via an oxygen atom or a sulfur atom, to form a ring. It is specifically desired that the groups are bonded together via a dimethylmethylene group to form a ring.

In the invention, it is desired that at least any one of $R^1$ to $R^{12}$ is a deuterium atom or a group that contains a deuterium atom, such as alkenyl group, aromatic hydrocarbon atom or aromatic heterocyclic group having a deuterium atom as a substituent.

In the general formula (1), further, $A^1$ to $A^3$ are the portions where the triphenylamine skeletons are bonded together, and are single bonds or divalent hydrocarbon groups.

As the divalent hydrocarbon group, i.e., as the divalent group without containing hetero atom, there can be exemplified those represented by the following structural formulas (B) to (F).

[Chemical 9]

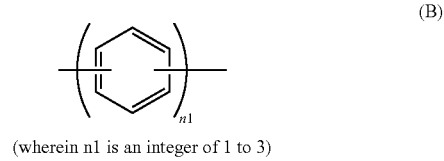

(B)

(wherein n1 is an integer of 1 to 3)

[Chemical 10]

(C)

[Chemical 11]

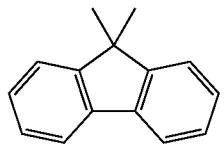

[Chemical 12]

—CH$_2$— (E)

[Chemical 13]

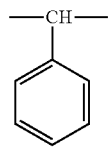 (F)

As the arylamine compound (X) having three or more triphenylamine skeletons used in the present invention, there can be concretely exemplified the following compounds (1-1) to (1-20). Among them, however, the triarylamine (having four triphenylamine skeletons) represented by the above general formula (1) is specifically desired.

[Chemical 14]

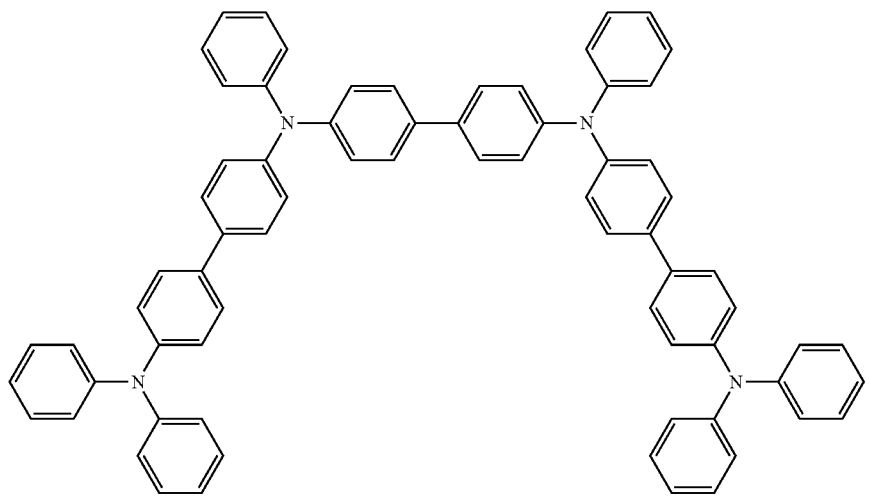

(1-1)

[Chemical 15]

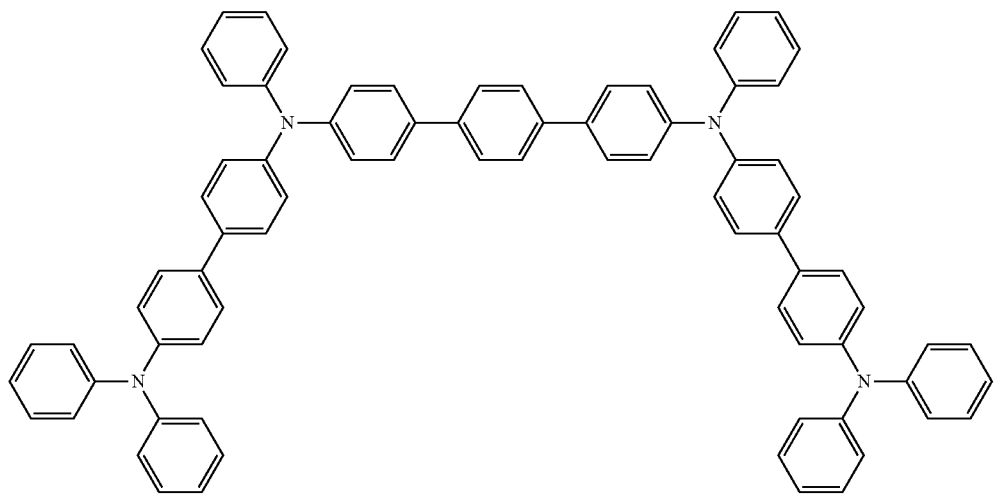

(1-2)

[Chemical 16]
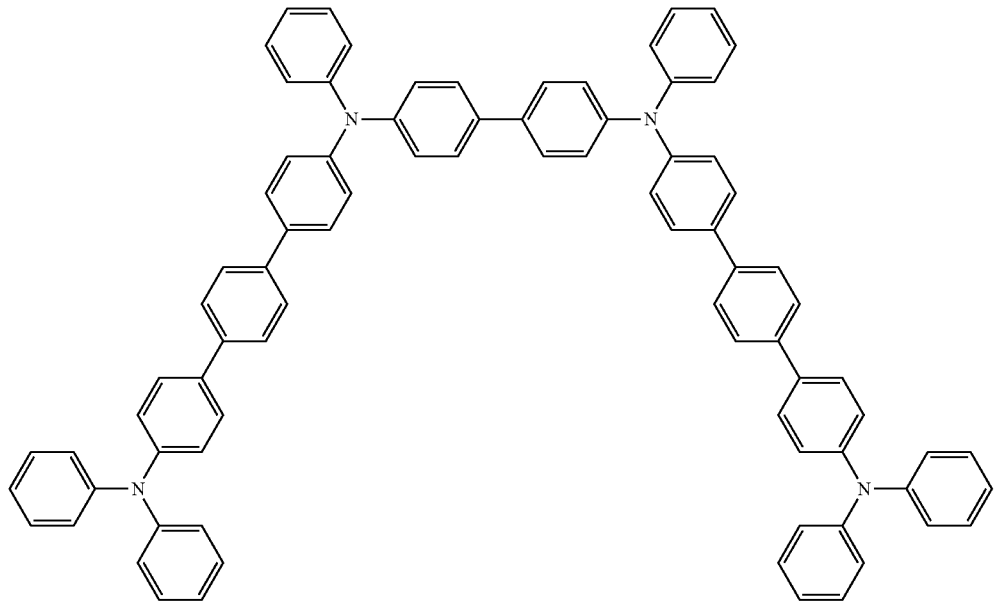
(1-3)
[Chemical 17]
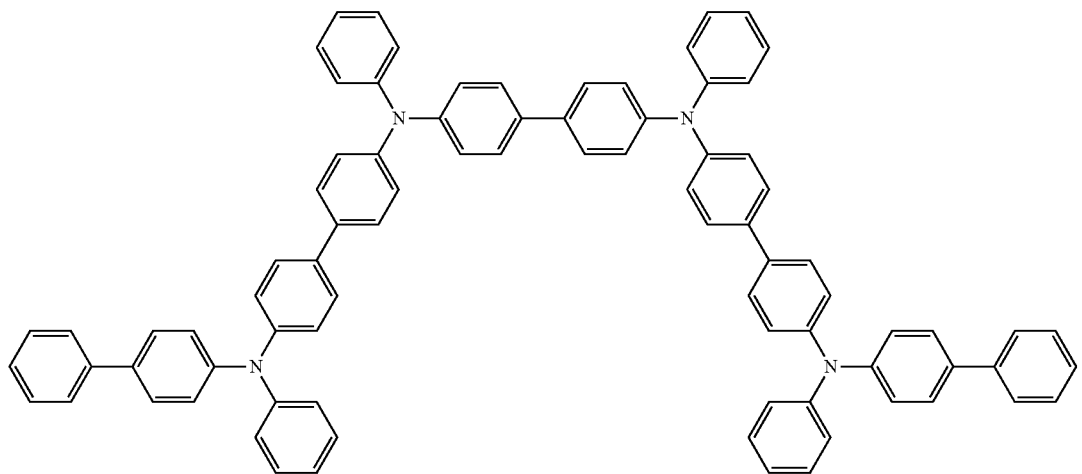
(1-4)

-continued
[Chemical 18]
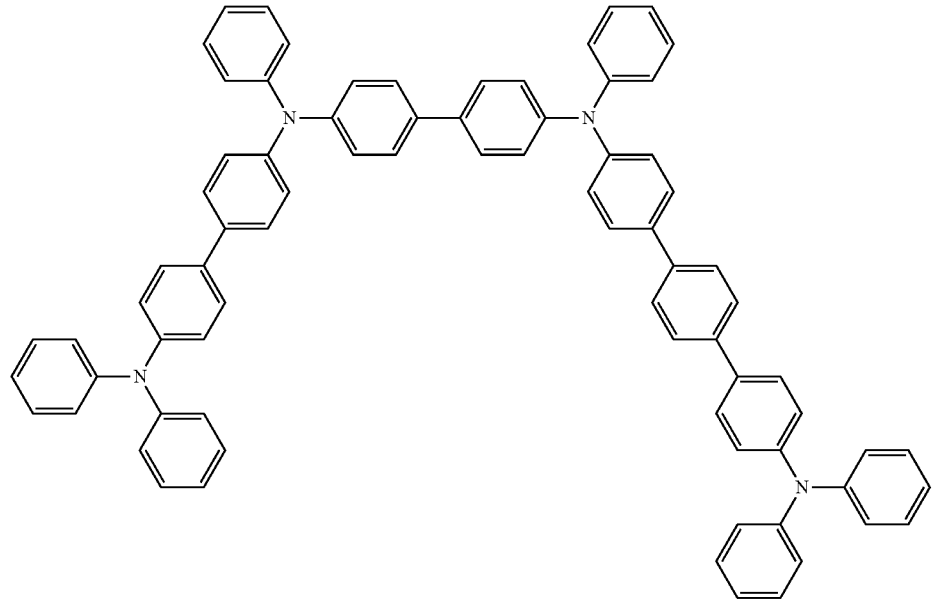
(1-5)
[Chemical 19]
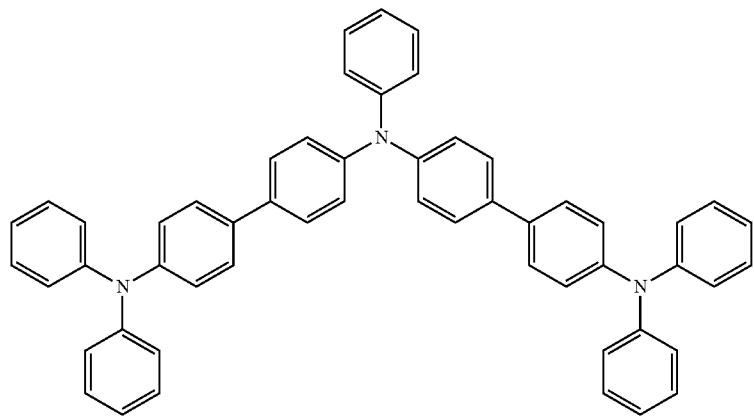
(1-6)

[Chemical 20]
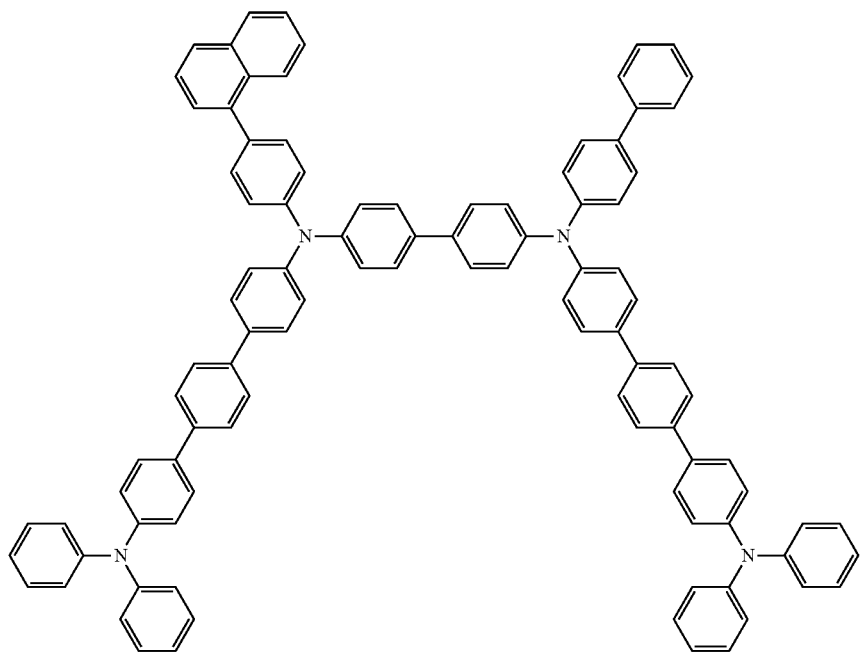
(1-7)
[Chemical 21]
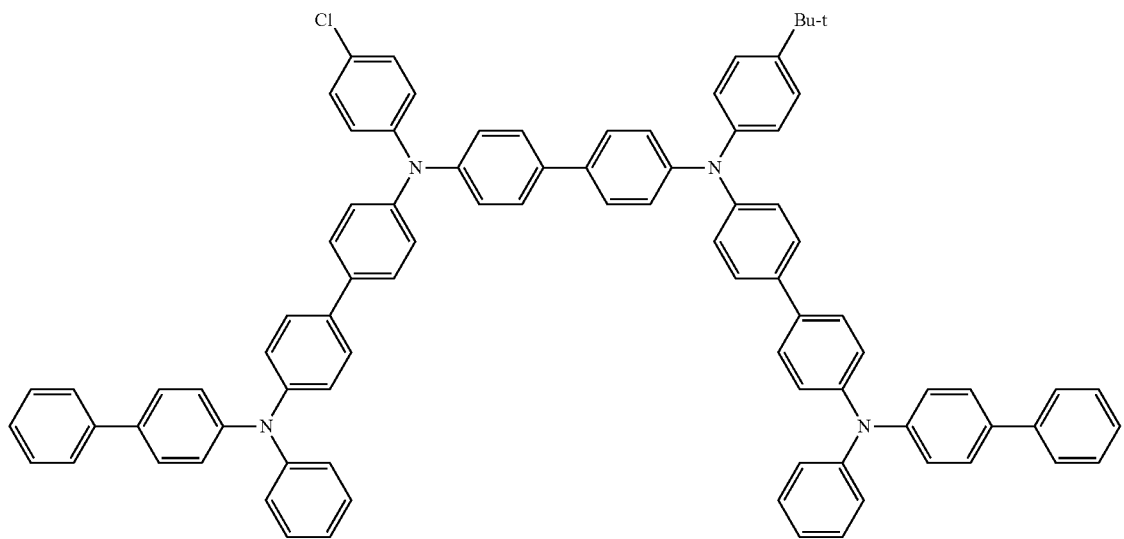
(1-8)

[Chemical 22]
(1-9)
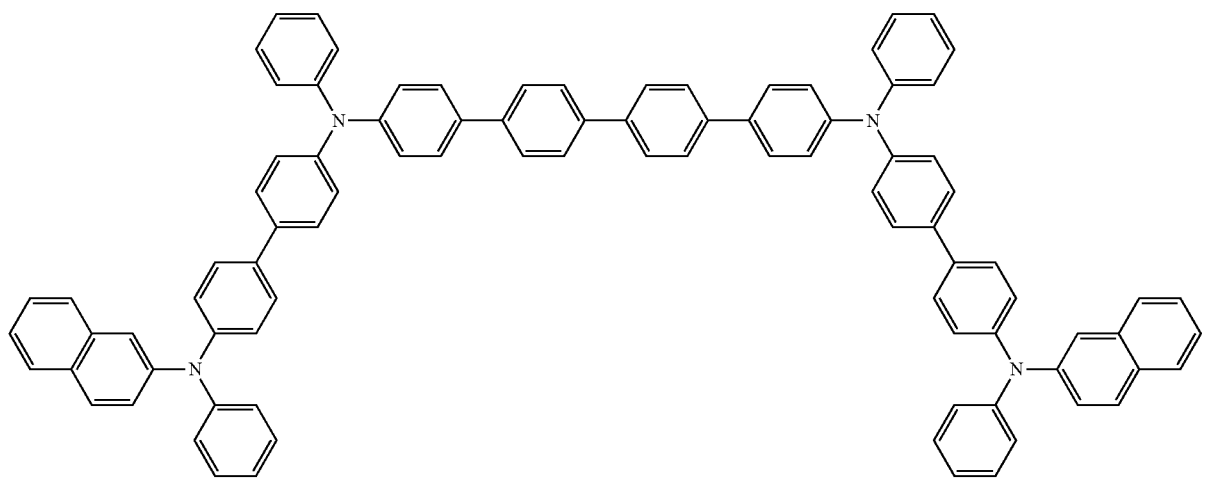
[Chemical 23]
(1-10)
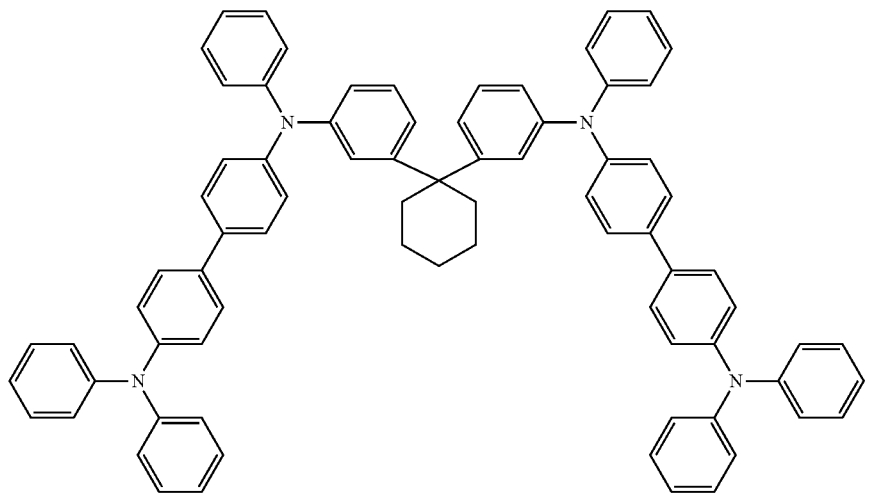
[Chemical 24]
(1-11)
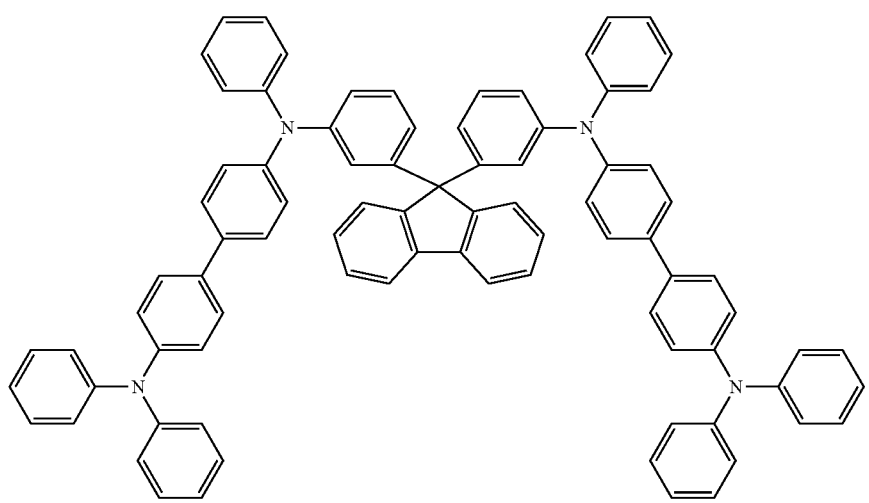

[Chemical 25]
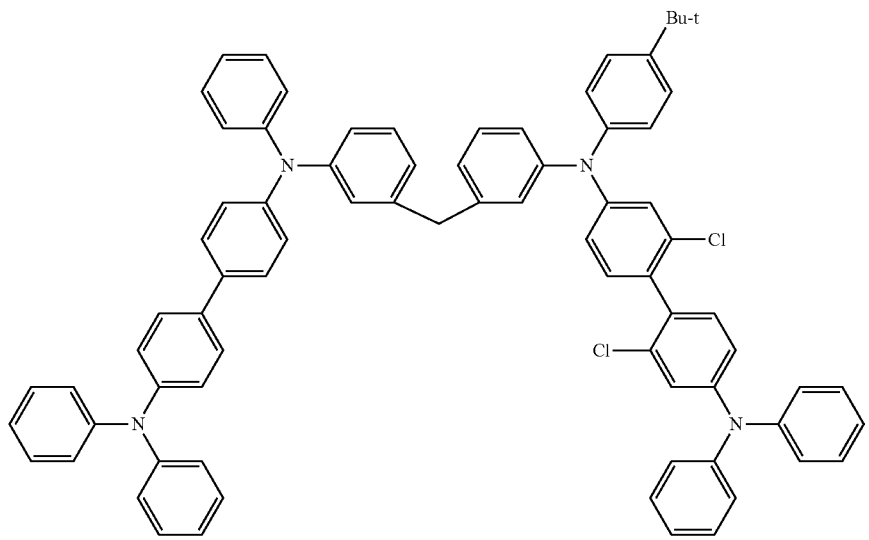
(1-12)
[Chemical 26]
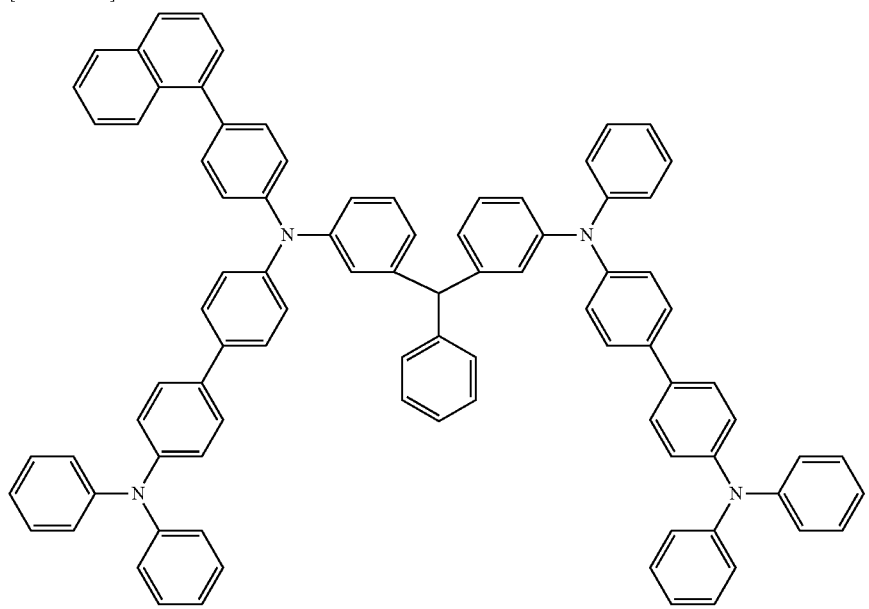
(1-13)
[Chemical 27]
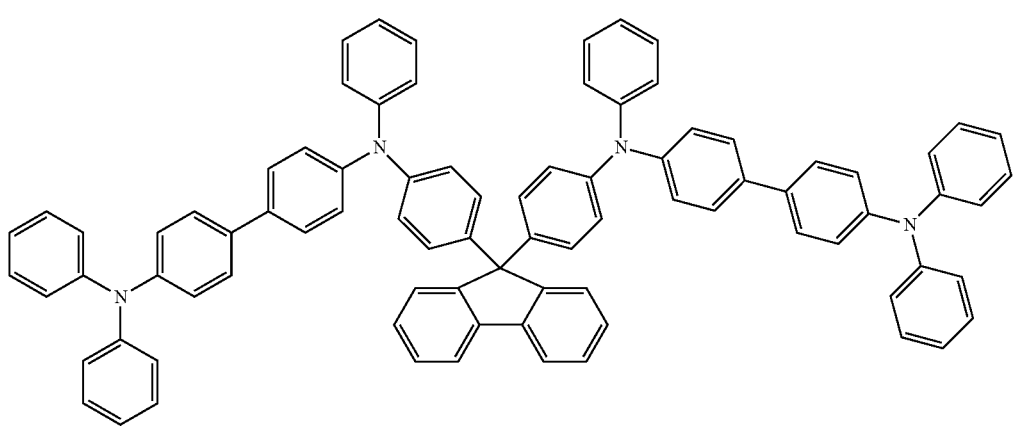
(1-14)

[Chemical 28]
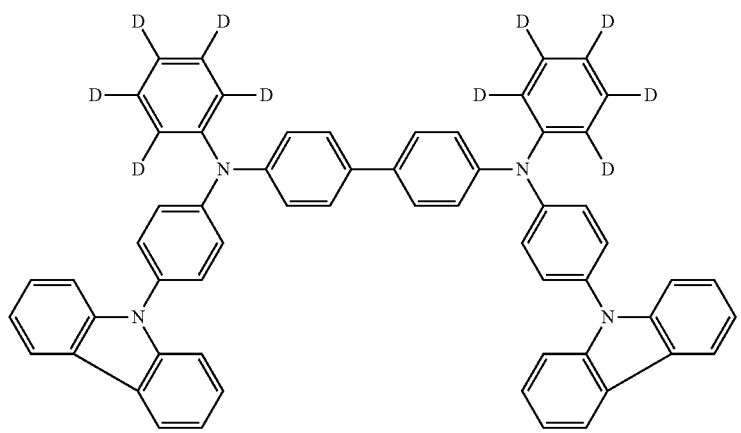
(1-15)
[Chemical 29]
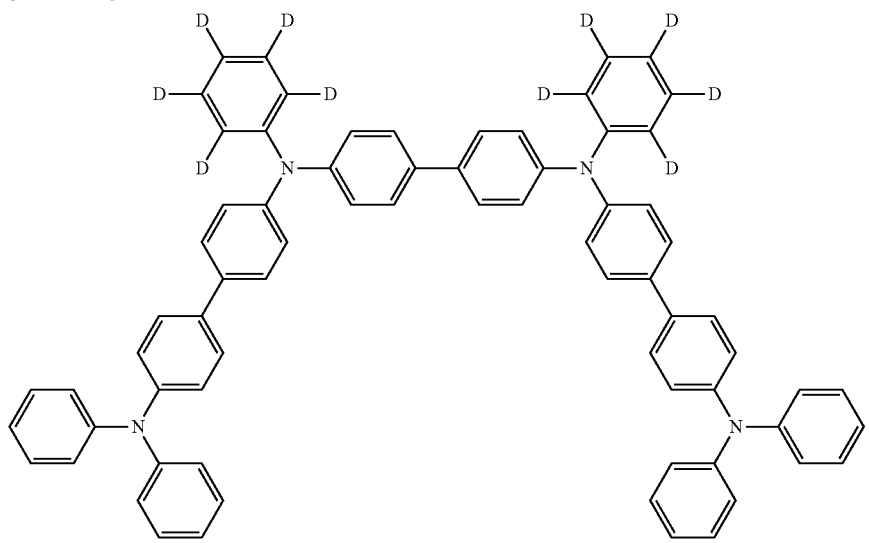
(1-16)
[Chemical 30]
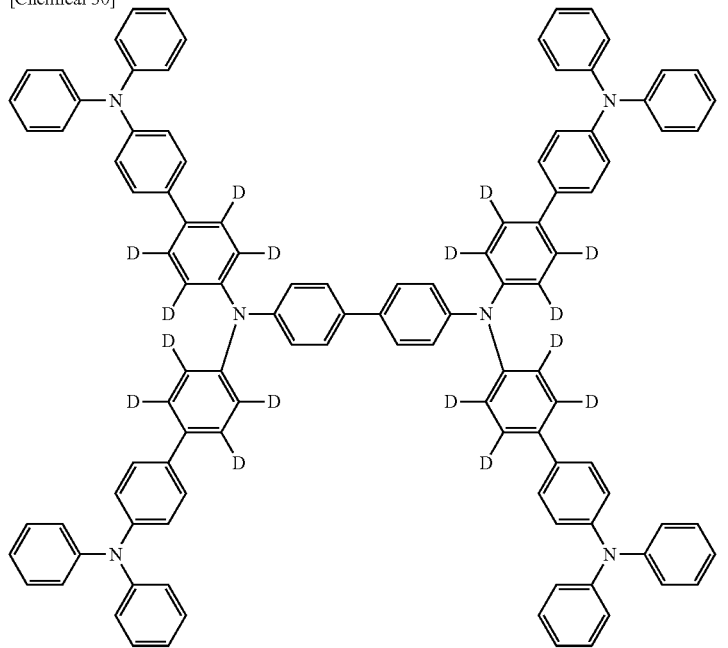
(1-17)

[Chemical 31]
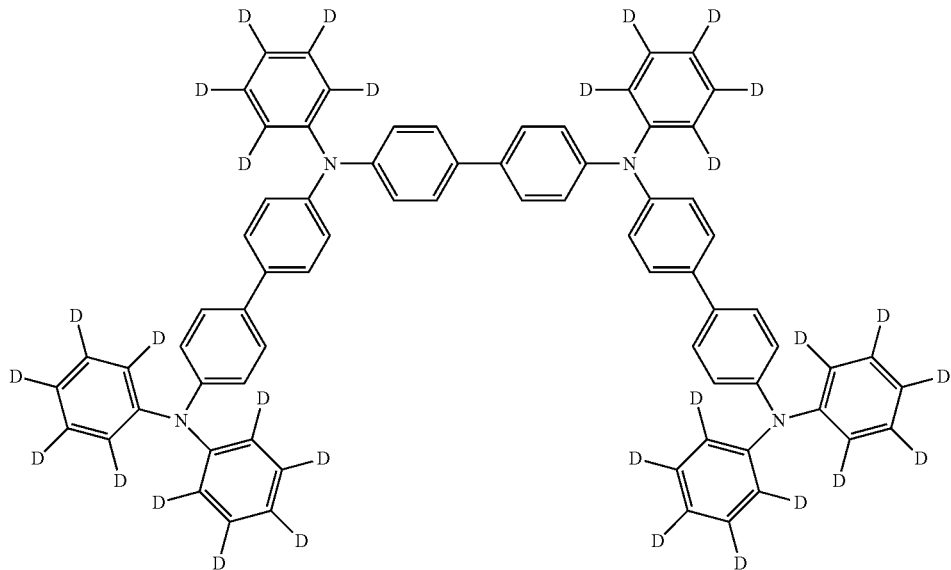
(1-18)
[Chemical 32]
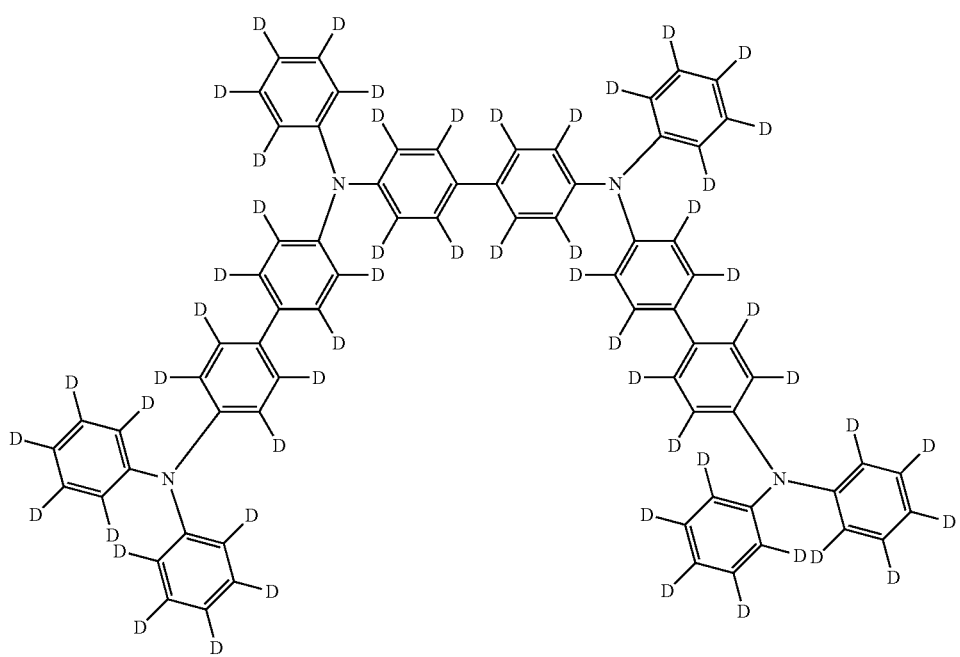
(1-19)

[Chemical 33]

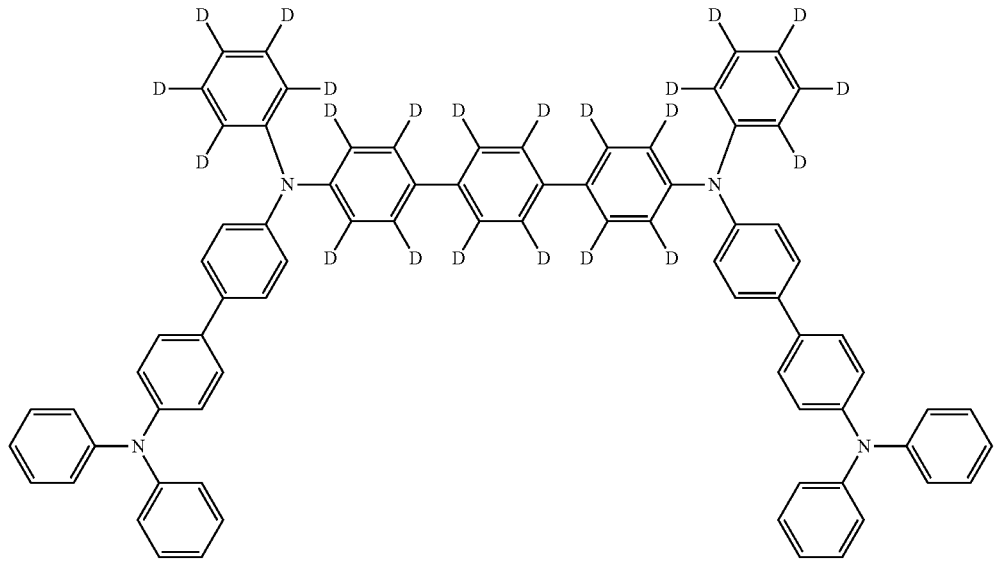

(1-20)

Arylamine Compound (Y):

The arylamine compound (Y) used in combination with the above arylamine compound (X) has two triphenylamine skeletons, and is represented, for example, by the following general formula (2) though not limited thereto only.

[Chemical 34]

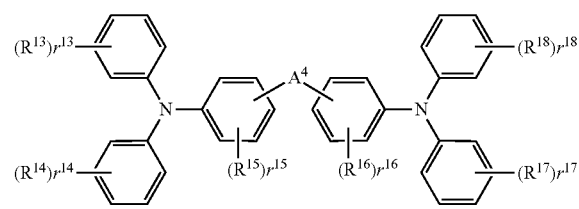

(2)

In the above general formula (2), $r^{13}$ to $r^{18}$ represent the numbers of the groups $R^{13}$ to $R^{18}$ bonded to the benzene rings in the molecules, $r^{13}$, $r^{14}$, $r^{17}$ and $r^{18}$ being integers of 0 to 5, and $r^{15}$ and $r^{16}$ being integers of 0 to 4. Namely, the values $r^{13}$ to $r^{18}$ that are 0s mean that none of the groups $R^{13}$ to $R^{18}$ have been bonded to the benzene rings.

The groups $R^{13}$ to $R^{18}$ may or may not be the same, and are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon groups, unsubstituted or substituted aromatic hydrocarbon groups, or unsubstituted or substituted aromatic heterocyclic groups. Further, if some of the groups $R^{13}$ to $R^{18}$ are present in plural numbers ($r^{13}$ to $r^{18}$ are 2 or more), they may be bonded together to form a ring.

Among the above groups $R^{13}$ to $R^{18}$, the unsubstituted alkyl group having 1 to 6 carbon atoms or the unsubstituted alkenyl groups having 2 to 6 carbon atoms may be of the form of a straight chain or may be branched, and is concretely the same alkyl group or the alkenyl group as the one exemplified above for $R^1$ to $R^{12}$.

Concrete examples of the aromatic hydrocarbon group or the aromatic heterocyclic group will be the same groups as those of the case of $R^1$ to $R^{12}$.

Further, the above alkenyl group, aromatic hydrocarbon group and aromatic heterocyclic group may have a substituent which can be the same substituents as those exemplified for $R^1$ to $R^{12}$.

Further, if some of the groups $R^{13}$ to $R^{18}$ are present in plural numbers and are bonded together to form ring, they may be singly bonded together to form a ring, or may be bonded together via a methylene group that may have a substituent, or via an oxygen atom or a sulfur atom, to form a ring. It is specifically desired that the groups are bonded together via a dimethylmethylene group to form a ring.

In the invention, it is desired that at least any one of $R^{13}$ to $R^{18}$ is a deuterium atom or a group that contains a deuterium atom (e.g., alkenyl group, aromatic hydrocarbon atom or aromatic heterocyclic group having a deuterium atom as a substituent).

In the general formula (2), further, $A^4$ is a portion where the triphenylamine skeletons are bonded together, and is a single bond or a divalent hydrocarbon group. As the divalent hydrocarbon group, there can be exemplified those represented by the above structural formulas (B) to (F).

As the arylamine compound (Y) represented by the above general formula (2), there can be preferably exemplified, N,N'-Diphenyl-N,N'-di(m-tolyl)benzidine (TPD), N,N'-Diphenyl-N,N'-di(α-naphthyl)benzidine (NPD), 1,1-Bis[4-(di-4-tolylamino)phenyl]cyclohexane (TAPC), as well as the following compounds (2-1) to (2-26).

[Chemical 35]
(2-1)
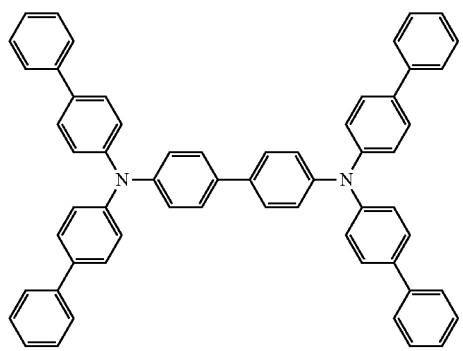
[N,N,N',N'-Tetrabiphenylylbenzidine]
[Chemical 36]
(2-2)
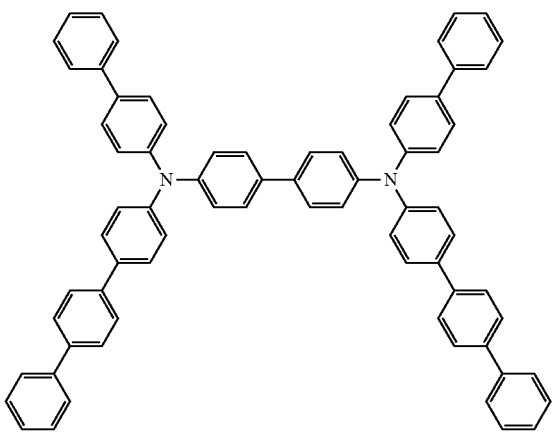
[Chemical 37]
(2-3)
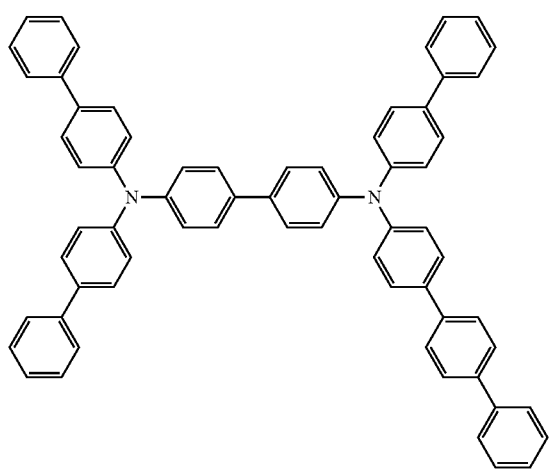
[Chemical 38]
(2-4)
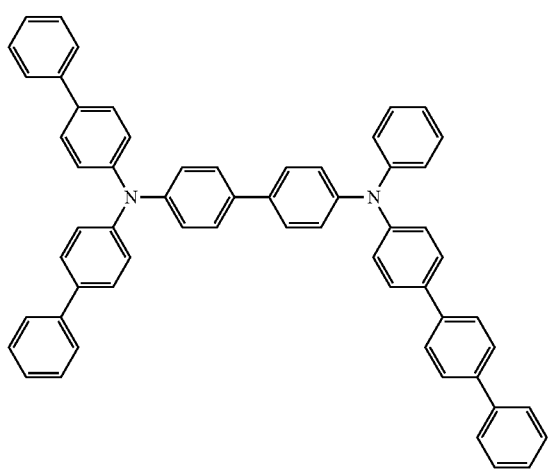
[Chemical 39]
(2-5)
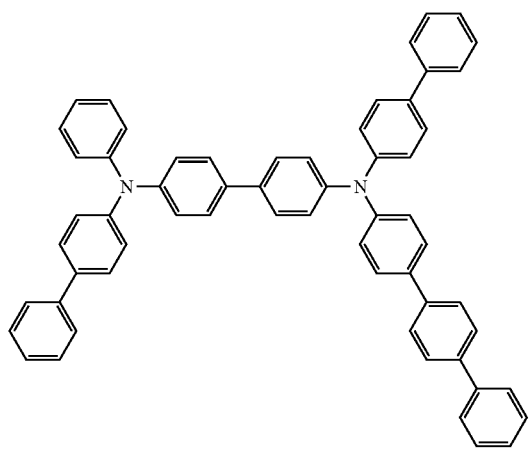
[Chemical 40]
(2-6)
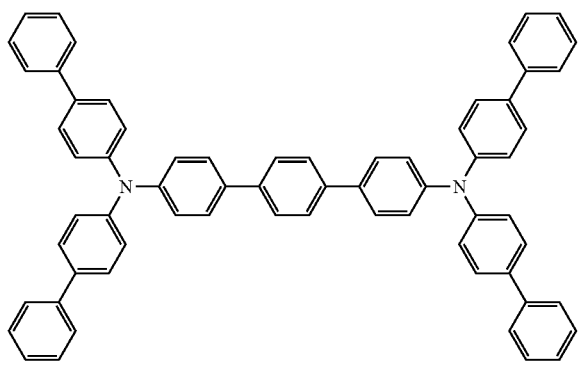

[Chemical 41]
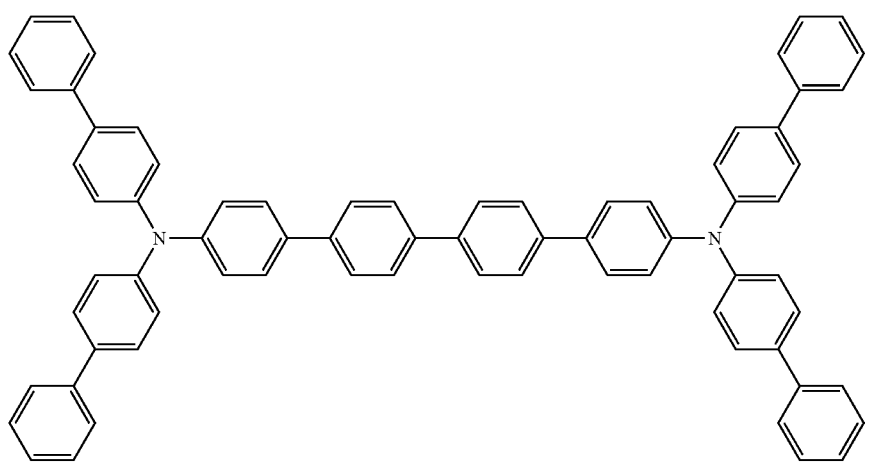
(2-7)
[Chemical 42]
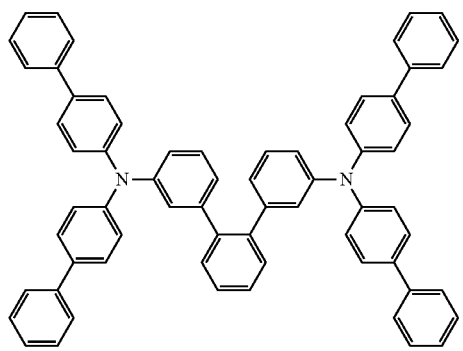
(2-8)
[Chemical 43]
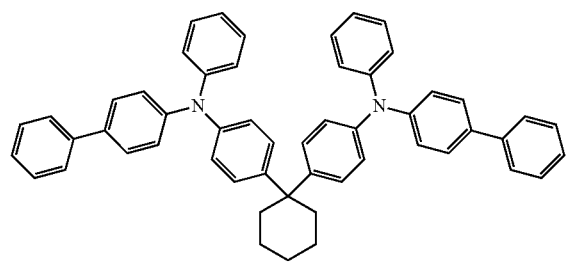
(2-9)
[Chemical 44]
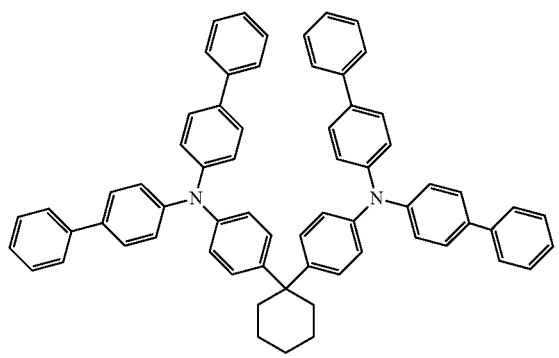
(2-10)
[Chemical 45]
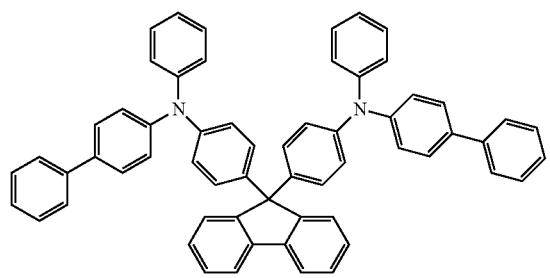
(2-11)

-continued
[Chemical 46]
(2-12)
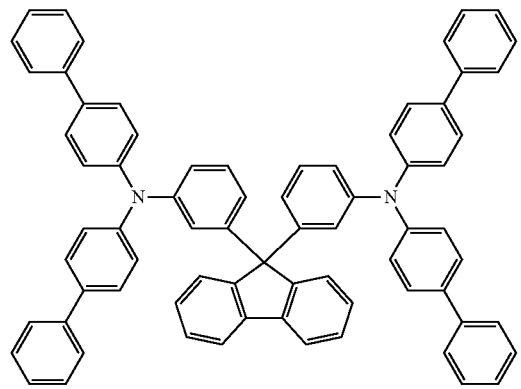
[Chemical 47]
(2-13)
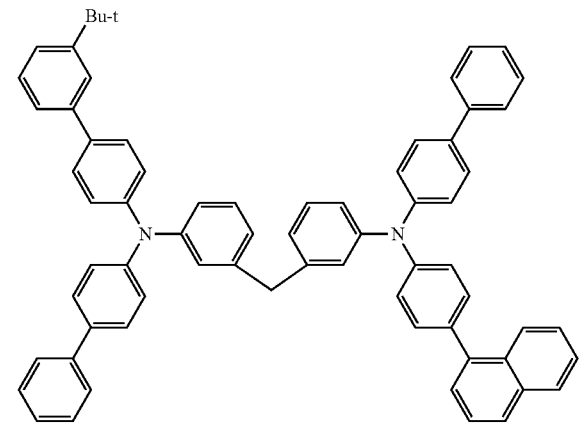
[Chemical 48]
(2-14)
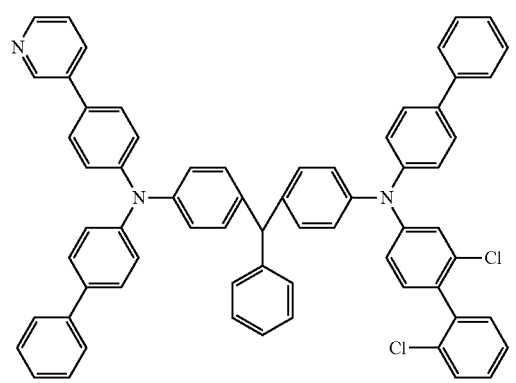
[Chemical 49]
(2-15)
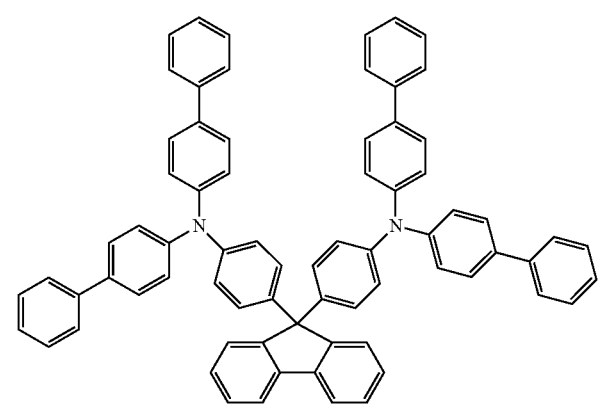
[Chemical 50]
(2-16)
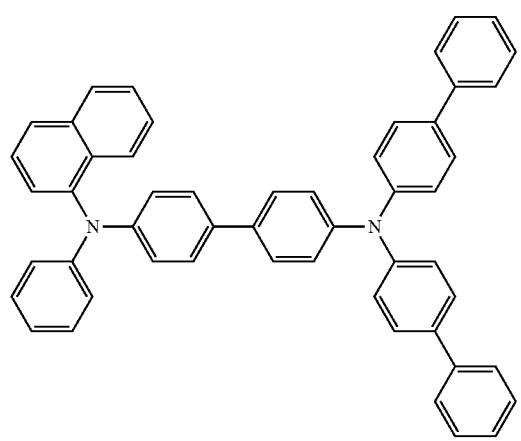
[Chemical 51]
(2-17)
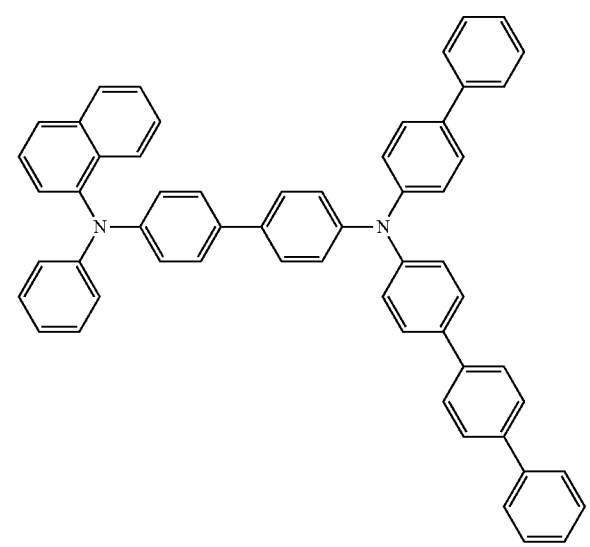

[Chemical 52]
(2-18)
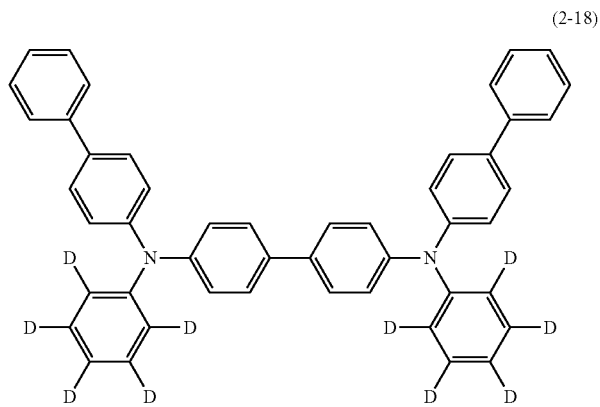
[Chemical 53]
(2-19)
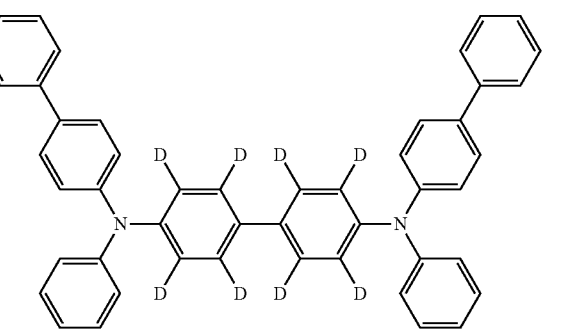
[Chemical 54]
(2-20)
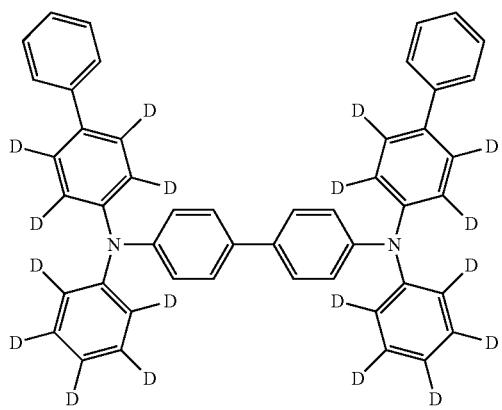
[Chemical 55]
(2-21)
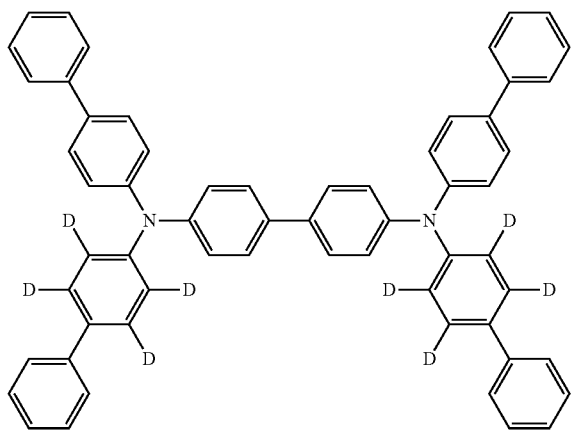
[Chemical 56]
(2-22)
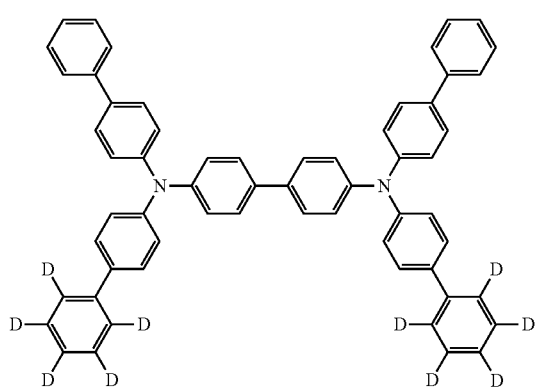
[Chemical 57]
(2-23)
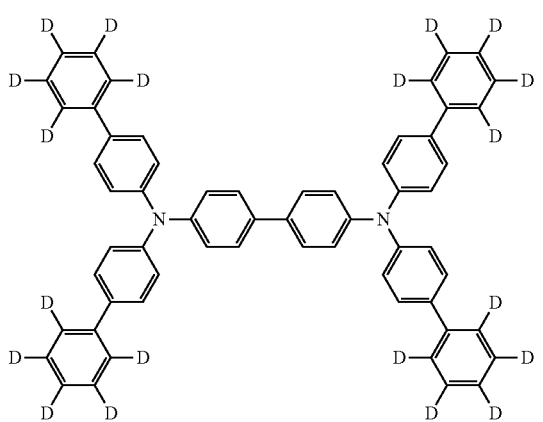

[Chemical 58]
(2-24)
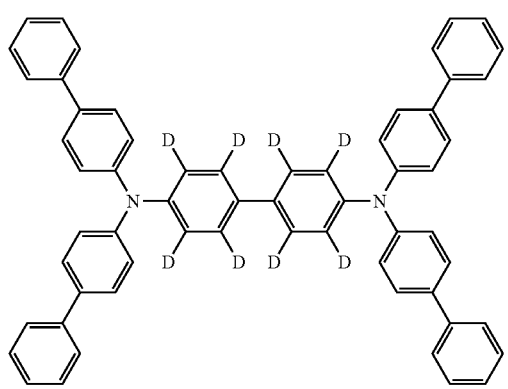
[Chemical 59]
(2-25)
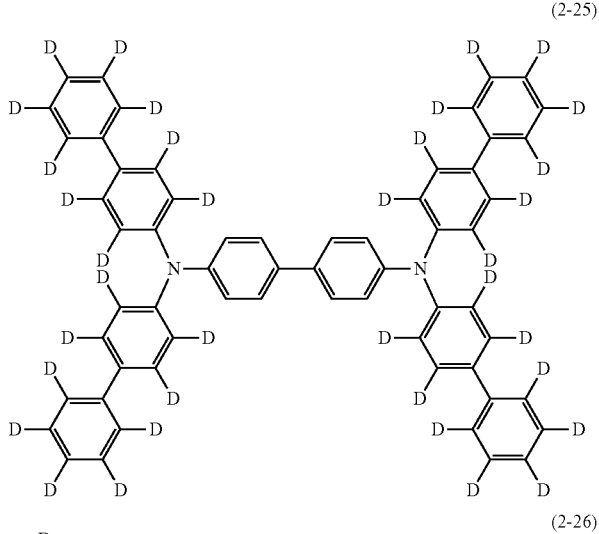
[Chemical 60]
(2-26)
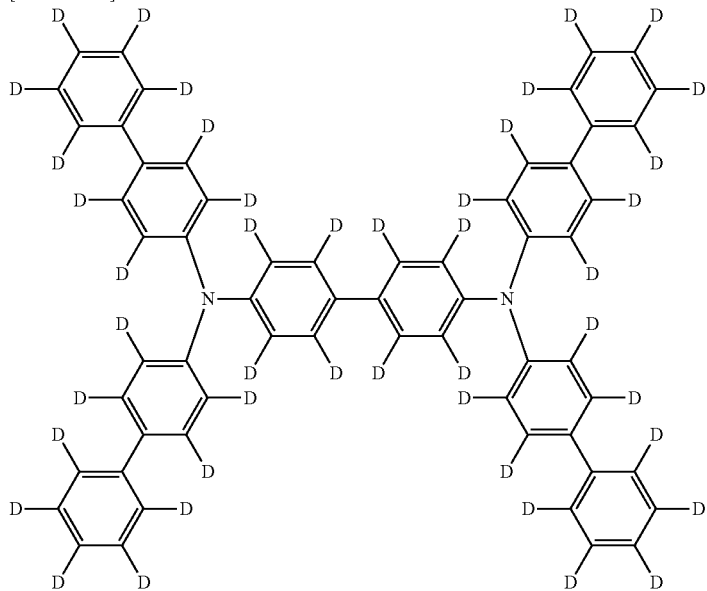
Further, though not represented by the general formula (2), the following compounds (2'-1) and (2'-2), too, can be favorably used as the arylamine compound (Y) having two triphenylamine skeletons.
[Chemical 61]
(2'-1)
[Chemical 62]
(2'-2)
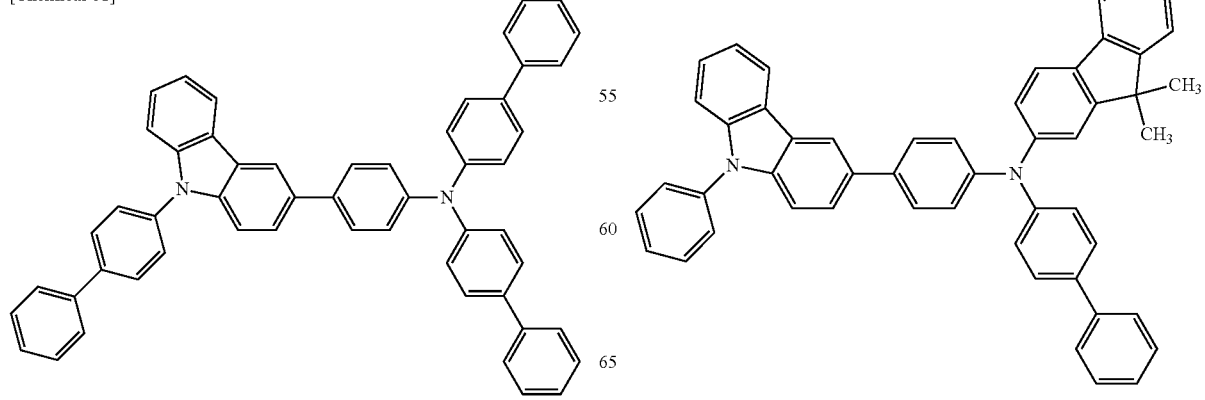

The above-mentioned arylamine compound (X) and the arylamine compound (Y) can be synthesized by the methods known per se (e.g., see patent documents 7 to 9).

The hole-transporting layer in the organic EL device of the present invention contains the above two kinds of arylamine compound (X) and arylamine compound (Y). Use of the two kinds of arylamine compounds (X) and (Y) makes it possible to attain a high hole drift speed, to maintain a high luminous efficiency and to lower the driving voltage. In addition to lowering the driving voltage, the hole-transporting layer remains stable in the form of a thin film enabling the organic EL device to feature a long life.

In the invention, the weight ratio (X:Y) of the arylamine compound (X) and the arylamine compound (Y) contained in the hole-transporting layer is, preferably, 1:9 to 6:4, more preferably, 1:9 to 4:6 and, most preferably, 1:9 to 2:8. Namely, when the hole-transporting layer is formed by using either one compound only, balance is not maintained between the hole drift speed and the electron drift speed, a high luminous efficiency is not attained as compared to when the two kinds of arylamine compounds are used in combination, and the driving voltage cannot be lowered.

The hole-transporting layer may contain materials that have heretofore been used for forming the conventional hole-transporting layers and may have a laminated structure of a lamination of layers formed by using known materials. For instance, a layer P-doped with a trisbromophenylaminehexachloroantimony or the like may be laminated, as an independent layer, on the layer that contains the above two kinds of arylamine compounds.

In the organic EL device of the present invention, the hole-transporting layer containing the above two kinds of arylamine compounds has a thickness which is, usually, about 40 to about 60 nm. Even if the thickness is increased to, for example, 100 nm or more, however, an increase in the driving voltage is suppressed since the organic EL device becomes luminous on a low driving voltage. This offers a high degree of freedom in selecting the thickness of the hole-transporting layer, and a practical driving voltage can be maintained with a thickness of, for example, 20 to 300 nm and, specifically, 20 to 200 nm.

The hole-transporting layer is desirably formed relying on the vacuum coevaporation by using a mixed gas containing the above-mentioned two kinds of arylamine compound (X) and arylamine compound (Y), but can also be formed by a known method such as spin-coating method or ink-jet method.

<Luminous Layer>

The luminous layer is the same as the one used in the conventional organic EL devices, and is formed by a known method such as vacuum evaporation method, spin-coating method or ink-jet method depending on the kind of the material that is used.

The luminous layer can be formed by using luminous materials, for example, metal complexes of quinolinol derivatives such as $Alq_3$, complexes of various metals such as zinc, beryllium and aluminum, anthracene derivative, bisstyrylbenzene derivative, pyrene derivative, oxazole derivative and polyparaphenylenevinylene derivative.

The luminous layer can also be formed by using a host material and a dopant material (guest material). As the host material, in this case, there can be used thiazole derivative, benzimidazole derivative, and polydialkylfluorene derivative in addition to the above-mentioned luminous materials. As the dopant material, there can be used quinacridone, cumalin, rubrene, perylene and derivatives thereof, benzopyran derivative, Rhodamine derivative and aminostyryl derivative.

As the guest material, further, there can be used a luminous phosphor. As the luminous phosphor, there can be used a luminous phosphor of a metal complex of iridium or platinum. For instance, there can be used a green luminous phosphor such as $Ir(ppy)_3$, a blue luminous phosphor such as Flrpic or $Flr_6$, and a red luminous phosphor such as $Btp_2Ir$(acac).

As the host material, in this case, there can be used a hole injection/transport host material of a carbazole derivative, such as 4,4'-di(N-carbazolyl)biphenyl (CBP), TCTA or mCP, and there can be, further, used an electron-transporting host material such as p-bis(triphenylsilyl)benzene (UGH2) or 2,2',2"-(1,3,5-phenylene)-tris(1-phenyl-1H-benzimidazole) (TPBI). By using such host materials, it is allowed to fabricate an organic EL device of high performance.

To avoid the concentration quenching, the host material is desirably doped with the luminous phosphor in an amount in a range of 1 to 30% by weight relative to the whole luminous layer relying on the vacuum coevaporation.

The luminous layer is not limited to the one of a single-layer structure but may have a laminated structure of a lamination of layers formed by using the above-mentioned compounds.

<Electron-Transporting Layer>

The electron-transporting layer may be formed by using an electron-transporting material that has been known per se. There can be used metal complexes of quinolinol derivatives such as $Alq_3$, as well as a variety of metal complexes such as of zinc, beryllium and aluminum, triazole derivatives, triazine derivatives, oxadiazole derivatives, thiadiazole derivatives, carbodiimide derivatives, quinoxaline derivatives, phenanthroline derivatives and silole derivatives.

In the present invention, the electron-transporting layer is formed by a known method such as vacuum evaporation method, spin-coating method or ink-jet method depending on the kind of the material that is used.

The electron-transporting layer is not limited to the one of a single-layer structure but may have a laminated structure of a lamination of layers formed by using the above-mentioned compounds.

<Cathode>

As the cathode of the organic EL device of the invention, there is used a metal having a low work function, such as aluminum or an alloy having a lower work function, such as magnesium-silver alloy, magnesium-indium alloy or aluminum-magnesium alloy.

<Other Layers>

The organic EL device of the present invention may, as required, have any other layers so far as it has the above-mentioned basic structure. For instance, a hole injection layer may be provided between the anode and the hole-transporting layer, and an electron blocking layer may be provided between the hole-transporting layer and the luminous layer. Moreover, a hole-blocking layer may be provided between the luminous layer and the electron-transporting layer. Further, an electron injection layer may be provided between the electron-transporting and the cathode. These hole injection layer, electron-blocking layer, hole-blocking layer and electron injection layer may be formed by using the materials that have been known per se, and are formed by the known method such as vacuum evaporation, spin-coating method or ink-jet method depending on the kinds of the materials that are used.

Hole Injection Layer:

The hole injection layer is desirably formed by using the above-mentioned arylamine compound (X) between the anode and the hole-transporting layer. This is because the arylamine compound (X) has a very large hole mobility.

Electron Blocking Layer:

As the material for forming the electron blocking layer, there can be used various compounds having electron blocking power, and the following carbazole derivatives are representatively used.

4,4',4''-tri(N-carbazolyl)triphenylamine (TCTA),
9,9-bis[4-(carbazole-9-il)phenyl]fluorene,
1,3-bis(carbazole-9-il)benzene (mCP),
2,2-bis(4-carbazole-9-ilphenyl)adamantane (Ad-Cz).

As the material for forming the electron blocking layer, there can be further used compounds having a triphenylsilyl group and a triarylamine skeleton in the molecules as represented by a 9-[4-carbazole-9-il]phenyl]-9-[4-(triphenylsilyl)phenyl]-9H-fluorene in addition to using the above carbazole derivatives.

Hole Blocking Layer:

The hole blocking layer is formed by using a compound having a hole blocking action, such as a metal complex of a phenanthroline derivative like basocuproin (BCP) or quinolinol derivative like aluminum (III) bis(2-methyl-8-quinolinato)-4-phenylphenolate (BAlq), as well as various rare earth complexes, triazole derivatives, triazine derivatives and oxadiazole derivatives.

Electron Injection Layer:

The electron injection layer can be formed by using an alkali metal salt such as cesium fluoride or lithium fluoride, alkaline earth metal salt such as magnesium fluoride or a metal oxide such as aluminum oxide.

The above hole injection layer, electron blocking layer, hole blocking layer and electron injection layer, too, may respectively be formed in a single-layer structure or may comprise a plurality of layers.

EXAMPLES

The invention will now be concretely described below by way of Examples to which only, however, the invention is in no way limited.

In the following Examples, the weight ratios of the two kinds of compounds were calculated from the rates of vacuum evaporation (film-forming rates) of when the respective compounds were vacuum evaporated under the same conditions.

Example 1

An organic EL device of a structure shown in FIG. 1 was fabricated according to the procedure described below. Namely, the organic EL device has a structure in which a transparent anode 2 (ITO electrode), a hole injection layer 3, a hole-transporting layer 4, a luminous layer 5, an electron-transporting layer 6, an electron injection layer 7 and a cathode (aluminum electrode) 8 are formed by vacuum evaporation in this order on a glass substrate 1.

First, the glass substrate 1 on which the ITO (indium tin oxide) film has been formed in a thickness of 150 nm was washed with ultrasonic waves in an isopropyl alcohol for 20 minutes and was, thereafter, dried on a hot plate heated at 200° C. for 10 minutes followed by a treatment with UV ozone for 5 minutes. Thereafter, the glass substrate with ITO was placed in a vacuum evaporation machine, and the pressure therein was decreased down to 0.001 Pa or lower.

Next, the hole injection layer 3 was formed in a thickness of 20 nm by the vacuum evaporation by using the following compound (1-1) to cover the transparent anode 2.

On the hole injection layer 3, there was formed the hole-transporting layer 4 in a thickness of 40 nm by the two-way vacuum evaporation by using the following compound (1-1) and the compound (2-1) at such deposition rates that the weight ratio thereof was 20:80.

On the hole-transporting layer 4, there was formed the luminous layer 5 in a thickness of 30 nm by the two-way vacuum deposition by using the following compound (3) and the compound (4) at such deposition rates that the weight ratio thereof was 5:95.

On the luminous layer 5, there was formed the electron-transporting layer 6 by vacuum evaporating the Alq$_3$ in a thickness of 30 nm.

On the electron-transporting layer 6, there was formed the electron injection layer 7 by vacuum evaporating the lithium fluoride in a thickness of 0.5 nm.

Finally, the cathode 8 was formed by vacuum evaporating aluminum in a thickness of 150 nm.

The thus fabricated organic EL device was measured for its properties in the atmosphere at normal temperature. Table 1 summarizes the measured results of luminous properties of when a DC voltage was applied to the organic EL device.

[Chemical 63]

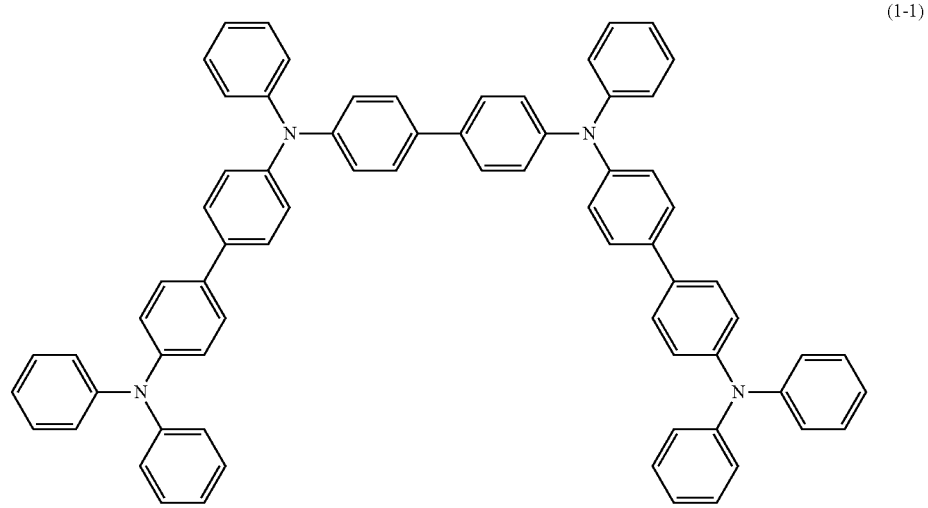

(1-1)

-continued

[Chemical 64]

(2-1)

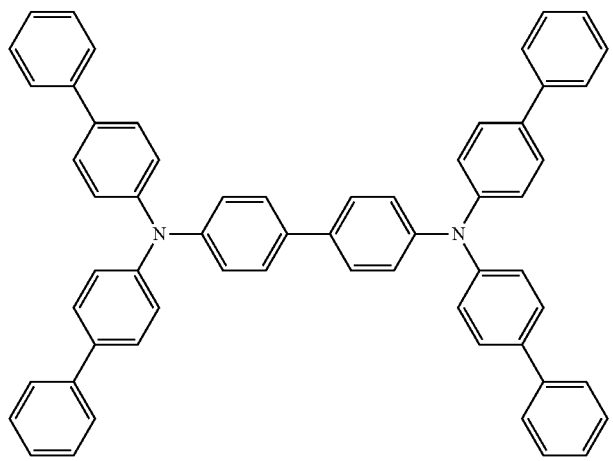

[Chemical 65]

(3)

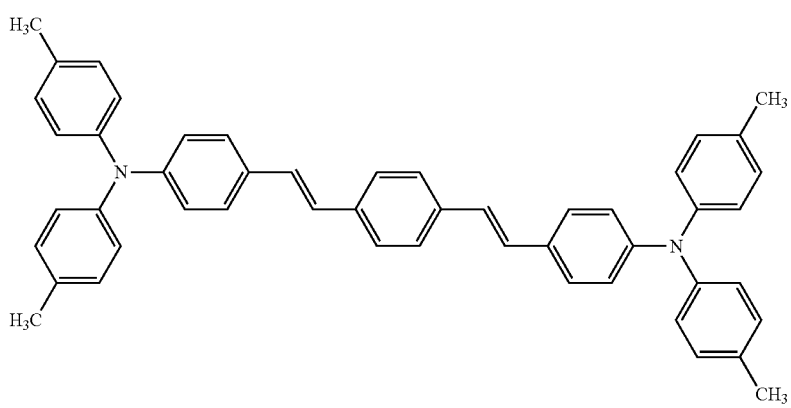

[Chemical 66]

(4)

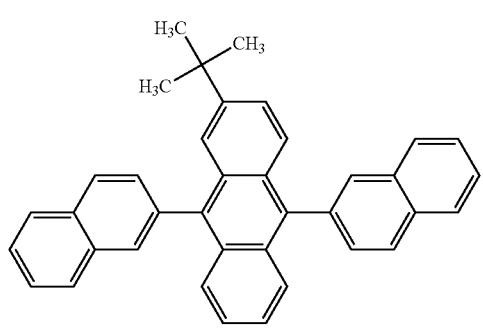

Example 2

An organic EL device was fabricated under the same conditions as in Example 1 but forming the hole-transporting layer 4 in a thickness of 40 nm by the two-way vacuum evaporation by using the above compound (1-1) and the compound (2-1) at such deposition rates that the weight ratio thereof was 10:90.

The thus fabricated organic EL device was measured for its properties in the atmosphere at normal temperature. Table 1 summarizes the measured results of luminous properties of when a DC voltage was applied to the organic EL device.

Example 3

An organic EL device was fabricated under the same conditions as in Example 1 but forming the hole-transporting layer 4 in a thickness of 40 nm by the two-way vacuum evaporation by using the above compound (1-1) and the compound (2-1) at such deposition rates that the weight ratio thereof was 40:60.

The thus fabricated organic EL device was measured for its properties in the atmosphere at normal temperature. Table 1 summarizes the measured results of luminous properties of when a DC voltage was applied to the organic EL device.

Example 4

An organic EL device was fabricated under the same conditions as in Example 1 but forming the hole-transporting layer 4 in a thickness of 40 nm by the two-way vacuum evaporation by using the above compound (1-1) and the compound (2-1) at such deposition rates that the weight ratio thereof was 60:40.

The thus fabricated organic EL device was measured for its properties in the atmosphere at normal temperature. Table 1 summarizes the measured results of luminous properties of when a DC voltage was applied to the organic EL device.

Comparative Example 1

For comparison, an organic EL device was fabricated under the same conditions as in Example 1 but forming the hole-transporting layer 4 in a thickness of 40 nm by using the above compound (2-1).

The thus fabricated organic EL device was measured for its properties in the atmosphere at normal temperature. Table 1 summarizes the measured results of luminous properties of when a DC voltage was applied to the organic EL device.

Comparative Example 2

For comparison, an organic EL device was fabricated under the same conditions as in Example 1 but forming the hole-transporting layer 4 in a thickness of 40 nm by using the above compound 1-1.

The thus fabricated organic EL device was measured for its properties in the atmosphere at normal temperature. Table 1 summarizes the measured results of luminous properties of when a DC voltage was applied to the organic EL device.

Comparative Example 3

For comparison, an organic EL device was fabricated under the same conditions as in Example 1 but forming the hole-transporting layer 4 in a thickness of 40 nm by the two-way vacuum evaporation by using the above compound (1-1) and the compound (2-1) at such deposition rates that the weight ratio thereof was 80:20.

The thus fabricated organic EL device was measured for its properties in the atmosphere at normal temperature. Table 1 summarizes the measured results of luminous properties of when a DC voltage was applied to the organic EL device.

TABLE 1

| | Weight ratio compound (1-1):compound (2-1) | Voltage [V] (@10 mA/cm$^2$) | Luminous efficiency [cd/A] | Power efficiency [lm/W] (@10 mA/cm$^2$) |
|---|---|---|---|---|
| Ex. 1 | 20:80 | 5.0 | 9.1 | 5.6 |
| Ex. 2 | 10:90 | 5.0 | 8.9 | 5.5 |
| Ex. 3 | 40:60 | 5.0 | 8.9 | 5.5 |
| Ex. 4 | 60:40 | 4.9 | 8.6 | 5.4 |
| Comp. Ex. 1 | 0:100 | 5.8 | 8.3 | 4.4 |
| Comp. Ex. 2 | 100:0 | 5.2 | 7.5 | 4.4 |
| Comp. Ex. 3 | 80:20 | 5.4 | 7.6 | 4.3 |

As shown in Table 1, when the electric current was flown at a density of 10 mA/cm$^2$, the driving voltages were 4.9 to 5.0 V in the cases of the devices of Examples 1 to 4, and were lower than those of 5.2 to 5.8 V of the cases of the devices of Comparative Examples 1 to 3. The luminous efficiencies were 8.6 to 9.1 cd/A in the cases of the devices of Examples 1 to 4, and were higher than those of 7.5 to 8.3 cd/A of the cases of the devices of Comparative Examples 1 to 3. Therefore, the power efficiencies were 5.4 to 5.6 lm/W in the cases of the devices of Examples 1 to 4, and were very higher than those of 4.3 to 4.4 lm/W of the cases of the devices of Comparative Examples 1 to 3.

Example 5

An organic EL device was fabricated under the same conditions as in Example 1 but forming the hole-transporting layer 4 in a thickness of 40 nm by the two-way vacuum evaporation by using the following compound (1-16) and the compound (2-22) at such deposition rates that the weight ratio thereof was 20:80.

The thus fabricated organic EL device was measured for its properties in the atmosphere at normal temperature. Table 2 summarizes the measured results of luminous properties of when a DC voltage was applied to the organic EL device.

[Chemical 67]

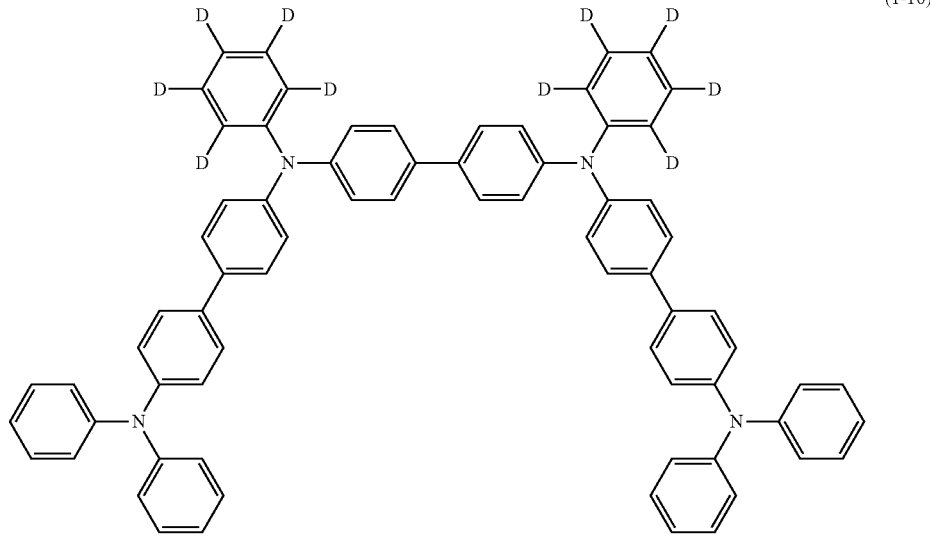

(1-16)

-continued

[Chemical 68]

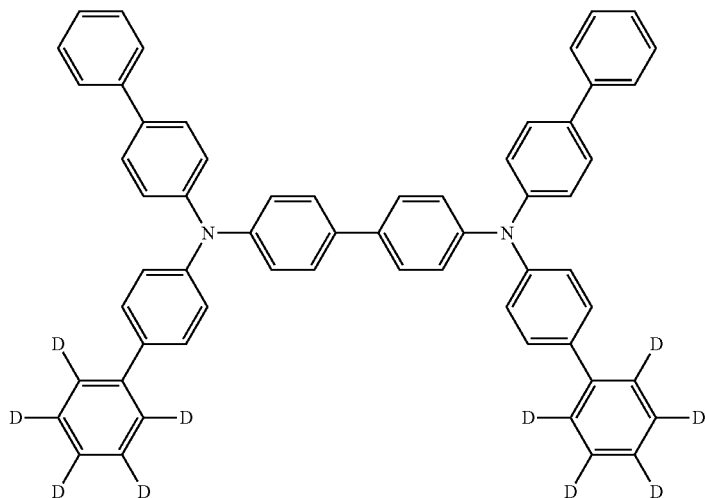

(2-22)

Example 6

An organic EL device was fabricated under the same conditions as in Example 5 but forming the hole-transporting layer 4 in a thickness of 40 nm by the two-way vacuum evaporation by using the above compound (1-16) and the compound (2-22) at such deposition rates that the weight ratio thereof was 10:90.

The thus fabricated organic EL device was measured for its properties in the atmosphere at normal temperature. Table 2 summarizes the measured results of luminous properties of when a DC voltage was applied to the organic EL device.

Comparative Example 4

For comparison, an organic EL device was fabricated under the same conditions as in Example 5 but forming the hole-transporting layer 4 in a thickness of 40 nm by using the above compound (2-22).

The thus fabricated organic EL device was measured for its properties in the atmosphere at normal temperature. Table 2 summarizes the measured results of luminous properties of when a DC voltage was applied to the organic EL device.

Comparative Example 5

For comparison, an organic EL device was fabricated under the same conditions as in Example 5 but forming the hole-transporting layer 4 in a thickness of 40 nm by using the above compound (1-16).

The thus fabricated organic EL device was measured for its properties in the atmosphere at normal temperature. Table 2 summarizes the measured results of luminous properties of when a DC voltage was applied to the organic EL device.

TABLE 2

|  | Weight ratio compound (1-16):compound (2-22) | Voltage [V] (@10 mA/cm$^2$) | Luminous efficiency [cd/A] (@10 mA/dm$^2$) | Power efficiency [lm/W] (@10 mA/cm$^2$) |
|---|---|---|---|---|
| Ex. 5 | 20:80 | 5.0 | 8.9 | 5.5 |
| Ex. 6 | 10:90 | 5.0 | 9.1 | 5.6 |

TABLE 2-continued

|  | Weight ratio compound (1-16):compound (2-22) | Voltage [V] (@10 mA/cm$^2$) | Luminous efficiency [cd/A] (@10 mA/dm$^2$) | Power efficiency [lm/W] (@10 mA/cm$^2$) |
|---|---|---|---|---|
| Comp. Ex. 4 | 0:100 | 5.2 | 8.3 | 4.9 |
| Comp. Ex. 5 | 100:0 | 5.3 | 7.8 | 4.5 |

As shown in Table 2, when the electric current was flown at a density of 10 mA/cm$^2$, the driving voltages were each 5.0 V in the cases of the devices of Examples 5 and 6, and were lower than those of 5.2 and 5.3 V of the cases of the devices of Comparative Examples 4 and 5. The luminous efficiencies were 8.9 and 9.1 cd/A in the cases of the devices of Examples 5 and 6, and were higher than those of 7.8 and 8.3 cd/A of the cases of the devices of Comparative Examples 4 and 5. Therefore, the power efficiencies were 5.5 and 5.6 lm/W in the cases of the devices of Examples 5 and 6, and were very higher than those of 4.5 and 4.9 lm/W of the cases of the devices of Comparative Examples 4 and 5.

<Evaluating the Life of the Organic EL Devices>

The organic EL devices of Example 1, Comparative Example 1 and Comparative Example 2 were measured for their lives to obtain results as summarized in Table 3. The electric current (W) for maintaining the device luminous at a brightness of 1000 cd/m$^2$ (this brightness was regarded to be an initial brightness of 100%) was set to be constant, and the time was measured until the brightness decreased down to 95%.

TABLE 3

|  | Weight ratio compound (1-1):compound (2-1) | Life of the device [hours] |
|---|---|---|
| Ex. 1 | 20:80 | 62 |
| Comp. Ex. 1 | 0:100 | 25 |
| Comp. Ex. 2 | 100:0 | 15 |

It is learned from Table 3 that the device of Example 1 has a life (62 hours) which is greatly lengthened compared to the lives (15 to 25 hours) of the devices of Comparative Examples 1 and 2.

It is learned that upon using the two kinds of specific arylamine compounds in combination, the organic EL device of the present invention possesses improved carrier balance, and helps attain a low driving voltage, a high luminous efficiency and an extended life compared to those of the conventional organic EL devices.

INDUSTRIAL APPLICABILITY

The organic EL device that uses the two kinds of specific arylamine compounds of the present invention features improved luminous efficiency, decreased driving voltage and improved durability, and finds a wide range of applications in the field of domestic electric appliances and lighting.

DESCRIPTION OF REFERENCE NUMERALS 1 glass substrate
2 transparent anode
3 hole injection layer
4 hole-transporting layer
5 luminous layer
6 electron-transporting layer
7 electron injection layer
8 cathode

The invention claimed is:

1. An organic electroluminescent device comprising, between an anode and a cathode, a hole-transporting layer, a luminous layer and an electron-transporting layer, wherein said hole-transporting layer contains an arylamine compound (X) having a molecular structure to which three or more triphenylamine skeletons are singly bonded or bonded through a divalent hydrocarbon group and an arylamine compound (Y) having a molecular structure to which two triphenylamine skeletons are singly bonded or bonded through a divalent hydrocarbon group,
wherein said arylamine compound (X) and said arylamine compound (Y) are contained in said hole-transporting layer at a weight ratio of X:Y=1:9 to 6:4.

2. The organic electroluminescent device according to claim 1, wherein said arylamine compound (X) is represented by the following general formula (1), wherein, $r^1$ to $r^{12}$, respectively, represent the numbers of $R^1$ to $R^{12}$, $r^1$, $r^2$, $r^5$, $r^8$, $r^{11}$ and $r^{12}$ being integers of 0 to 5, and $r^3$, $r^4$, $r^6$, $r^7$, $r^9$ and $r^{10}$ being integers of 0 to 4, $R^1$ to $R^{12}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups, or unsubstituted or substituted aromatic heterocyclic groups and among these groups, the groups bonded to the same benzene ring may be bonded together to form a ring, and $A^1$ to $A^3$, respectively, are single bonds or divalent hydrocarbon groups represented by the following structural formulas (B) to (F),

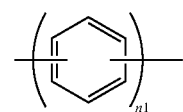

(B)

(wherein n1 is an integer of 1 to 3)

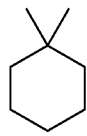

(C)

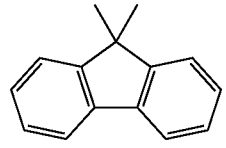

(D)

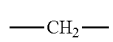

(E)

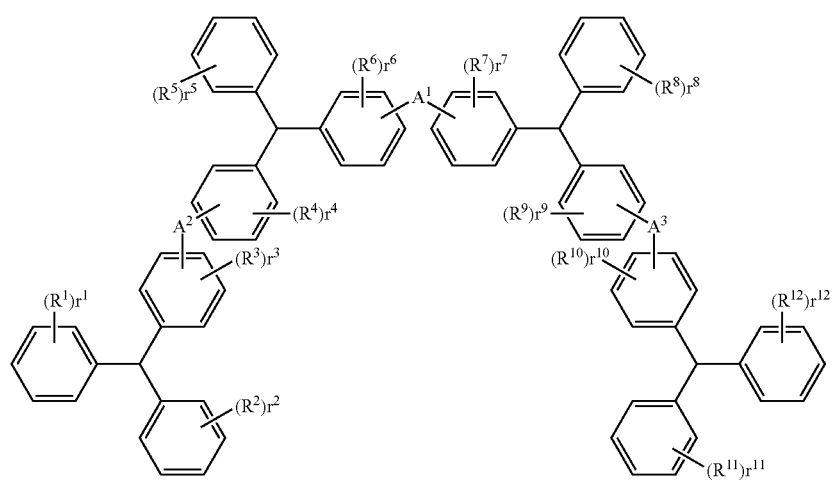

(1)

(F)

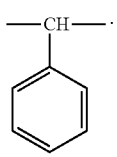

3. The organic electroluminescent device according to claim 2, wherein at least one of $R^1$ to $R^{12}$ in the above general formula (1) is a deuterium atom or a group that contains a deuterium atom.

4. The organic electroluminescent device according to claim 1, wherein said arylamine compound (Y) is represented by the following general formula (2), (2)

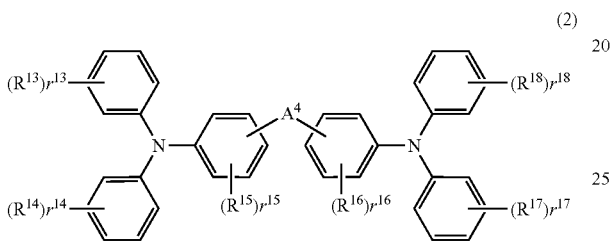

wherein, $r^{13}$ to $r^{18}$, respectively, represent the numbers of $R^{13}$ to $R^{18}$, $r^{13}$, $r^{14}$, $r^{17}$ and $r^{18}$ being integers of 0 to 5, and $r^{15}$ and $r^{16}$ being integers of 0 to 4, $R^{13}$ to $R^{18}$, respectively, are deuterium atoms, fluorine atoms, chlorine atoms, cyano groups, trifluoromethyl groups, unsubstituted alkyl groups having 1 to 6 carbon atoms, unsubstituted or substituted alkenyl groups having 2 to 6 carbon atoms, unsubstituted or substituted aromatic hydrocarbon groups, or unsubstituted or substituted aromatic heterocyclic groups and among these groups, the groups bonded to the same benzene ring may be bonded together to form a ring, and $A^4$ represents a single bond or a divalent hydrocarbon group represented by the following structural formulas (B) to (F), (B)

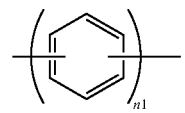

(wherein n1 is an integer of 1 to 3)

(C)

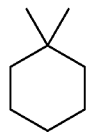

(D)

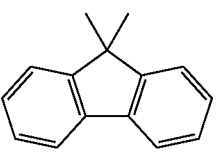

(E)

—CH$_2$—

(F)

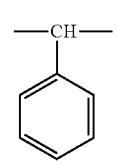

5. The organic electroluminescent device according to claim 4, wherein at least one of $R^{13}$ to $R^{18}$ in the above general formula (2) is a deuterium atom or a group that contains a deuterium atom.

6. The organic electroluminescent device of claim 1, wherein compound (x) and compound (Y) are contained in the hole transporting layer at a weight ratio of X:Y=1:9 to 4:6.

* * * * *

UNITED STATES PATENT AND TRADEMARK OFFICE
CERTIFICATE OF CORRECTION

PATENT NO. : 9,444,055 B2
APPLICATION NO. : 14/001560
DATED : September 13, 2016
INVENTOR(S) : N. Yokoyama et al.

It is certified that error appears in the above-identified patent and that said Letters Patent is hereby corrected as shown below:

In the Claims

Claim 2 (Column 47, Claim diagram), should read:

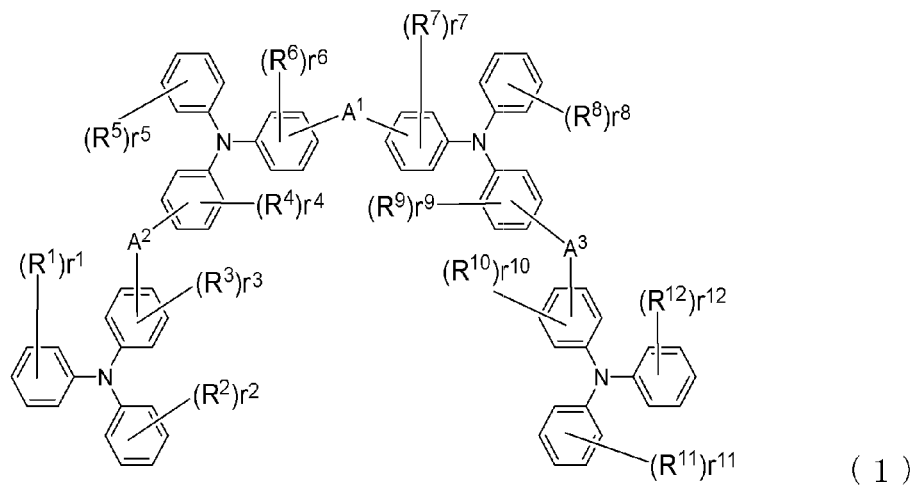

( 1 )

Signed and Sealed this
Thirtieth Day of May, 2017

Michelle K. Lee
*Director of the United States Patent and Trademark Office*